(12) United States Patent
Shelton, IV et al.

(10) Patent No.: US 11,974,825 B2
(45) Date of Patent: May 7, 2024

(54) MOTOR ADJUSTMENTS IN ABSENCE OF MOTOR DRIVE SIGNAL

(71) Applicant: Cilag GmbH International, Zug (CH)

(72) Inventors: Frederick E. Shelton, IV, Hillsboro, OH (US); Shane R. Adams, Lebanon, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/957,990

(22) Filed: Sep. 30, 2022

(65) Prior Publication Data

US 2024/0108420 A1 Apr. 4, 2024

Related U.S. Application Data

(60) Provisional application No. 63/411,445, filed on Sep. 29, 2022.

(51) Int. Cl.
*A61B 34/30* (2016.01)
*A61B 17/072* (2006.01)
*A61B 17/00* (2006.01)

(52) U.S. Cl.
CPC ........ *A61B 34/30* (2016.02); *A61B 17/07207* (2013.01); *A61B 2017/00398* (2013.01)

(58) Field of Classification Search
CPC .......................... A61B 34/30; A61B 17/07207
See application file for complete search history.

(56) References Cited

U.S. PATENT DOCUMENTS

| | | |
|---|---|---|
| 5,403,312 A | 4/1995 | Yates et al. |
| 5,817,084 A | 10/1998 | Jensen |
| 5,878,193 A | 3/1999 | Wang et al. |
| 6,132,368 A | 10/2000 | Cooper |
| 7,000,818 B2 | 2/2006 | Shelton, IV et al. |
| 7,422,139 B2 | 9/2008 | Shelton, IV et al. |
| 7,464,849 B2 | 12/2008 | Shelton, IV et al. |
| 7,524,320 B2 | 4/2009 | Tierney et al. |
| 7,670,334 B2 | 3/2010 | Hueil et al. |
| 7,753,245 B2 | 7/2010 | Boudreaux et al. |
| 7,845,537 B2 | 12/2010 | Shelton, IV et al. |

(Continued)

OTHER PUBLICATIONS

IEEE Std 802.3-2012 (Revision of IEEE Std 802.3-2008, published Dec. 28, 2012.

(Continued)

*Primary Examiner* — Nathaniel C Chukwurah
(74) *Attorney, Agent, or Firm* — Troutman Pepper Hamilton Sanders LLP

(57) ABSTRACT

Disclosed is a surgical system, comprising an end effector configurable between an open state and a clamped state. The end effector comprises a first jaw and a second jaw moveable relative to the first jaw. The surgical system further comprises a drive system, comprising a motor and a drive assembly movable by the motor to effect a tissue-treatment motion at the end effector. The surgical system further comprises a motor control system comprising motor control electronics. The motor control system is configured to transmit a motor drive signal that causes the motor to move the drive assembly to effect the tissue-treatment motion at the end effector and control the motor control electronics to modify the tissue-treatment motion independent of the motor drive signal.

20 Claims, 21 Drawing Sheets

(56) References Cited

U.S. PATENT DOCUMENTS

| | | |
|---|---|---|
| 7,980,443 B2 | 7/2011 | Scheib et al. |
| 8,210,411 B2 | 7/2012 | Yates et al. |
| 8,220,688 B2 | 7/2012 | Laurent et al. |
| 8,308,040 B2 | 11/2012 | Huang et al. |
| 8,393,514 B2 | 3/2013 | Shelton, IV et al. |
| 8,505,802 B2 | 8/2013 | Viola et al. |
| 8,561,870 B2 | 10/2013 | Baxter, III et al. |
| 8,608,045 B2 | 12/2013 | Smith et al. |
| 8,685,004 B2 | 4/2014 | Zemlock et al. |
| 8,733,613 B2 | 5/2014 | Huitema et al. |
| 9,016,540 B2 | 4/2015 | Whitman et al. |
| 9,050,083 B2 | 6/2015 | Yates et al. |
| 9,072,535 B2 | 7/2015 | Shelton, IV et al. |
| 9,101,358 B2 | 8/2015 | Kerr et al. |
| 9,345,481 B2 | 5/2016 | Hall et al. |
| 9,804,618 B2 | 10/2017 | Leimbach et al. |
| 9,808,246 B2 | 11/2017 | Shelton, IV et al. |
| 9,913,642 B2 | 3/2018 | Leimbach et al. |
| 9,987,095 B2 | 6/2018 | Chowaniec et al. |
| 10,159,483 B2 | 12/2018 | Beckman et al. |
| 10,368,865 B2 | 8/2019 | Harris et al. |
| 10,448,948 B2 | 10/2019 | Shelton, IV et al. |
| 10,639,037 B2 | 5/2020 | Shelton, IV et al. |
| 10,646,220 B2 | 5/2020 | Shelton, IV et al. |
| 10,695,057 B2 | 6/2020 | Shelton, IV et al. |
| 10,716,565 B2 | 7/2020 | Shelton, IV et al. |
| 10,758,226 B2 | 9/2020 | Weir et al. |
| 10,828,028 B2 | 11/2020 | Harris et al. |
| 10,835,245 B2 | 11/2020 | Swayze et al. |
| 10,842,523 B2 | 11/2020 | Shelton, IV et al. |
| 10,881,399 B2 | 1/2021 | Shelton, IV et al. |
| 10,888,321 B2 | 1/2021 | Shelton, IV et al. |
| 10,973,519 B2 | 4/2021 | Weir et al. |
| 11,324,501 B2 | 5/2022 | Shelton, IV et al. |
| 11,369,366 B2 | 6/2022 | Scheib et al. |
| 11,382,704 B2 | 7/2022 | Overmyer et al. |
| 11,419,630 B2 | 8/2022 | Yates et al. |
| 11,628,006 B2 | 4/2023 | Henderson et al. |
| 2007/0175955 A1 | 8/2007 | Shelton et al. |
| 2011/0017801 A1* | 1/2011 | Zemlok ............ A61B 17/07207 227/175.1 |
| 2011/0022032 A1* | 1/2011 | Zemlok ............ A61B 17/07207 606/1 |
| 2014/0263541 A1 | 9/2014 | Leimbach et al. |
| 2014/0263552 A1 | 9/2014 | Hall et al. |
| 2015/0209035 A1* | 7/2015 | Zemlok ............ A61B 17/07207 73/1.01 |
| 2017/0079642 A1 | 3/2017 | Overmyer et al. |
| 2019/0200981 A1 | 7/2019 | Harris et al. |
| 2019/0201027 A1 | 7/2019 | Shelton, IV et al. |
| 2021/0244407 A1 | 8/2021 | Shelton, IV et al. |

OTHER PUBLICATIONS

"ATM-MPLS Network Interworking Version 2.0, af-aic-0178.001" ATM Standard, The ATM Forum Technical Committee, published Aug. 2003.

\* cited by examiner

MOTOR ADJUSTMENTS IN ABSENCE OF MOTOR DRIVE SIGNAL

CROSS-REFERENCE TO RELATED APPLICATIONS

This application claims the benefit under 35 U.S.C. § 119(e) to U.S. Provisional Patent Application Ser. No. 63/411,445, titled METHOD FOR CONTROLLING SURGICAL SYSTEM DURING TISSUE TREATMENT MOTION, filed Sep. 29, 2022, the disclosure of which is herein incorporated by reference in its entirety.

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
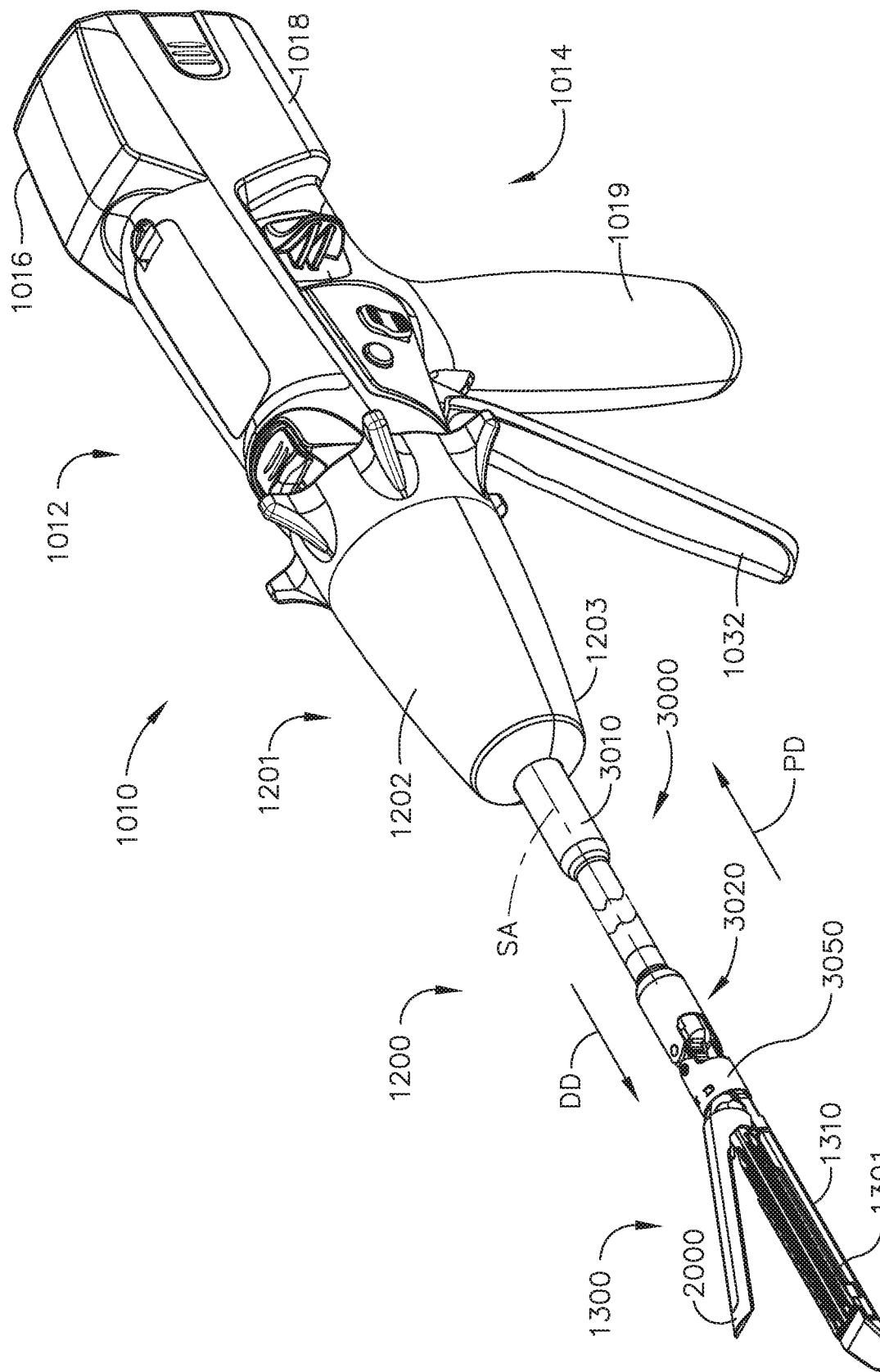
FIG. 1 is a perspective view of a powered surgical stapling system.

Applicant of the present application owns the following U.S. patent applications that were filed on Sep. 30, 2022 herewith and which are each herein incorporated by reference in their respective entireties:

U.S. patent application Ser. No. 17/957,917, titled METHOD FOR CONTROLLING SURGICAL SYSTEM DURING TISSUE TREATMENT MOTION;

U.S. patent application Ser. No. 17/957,923, titled ADAPTING TISSUE TREATMENT MOTION PARAMETERS BASED ON SITUATIONAL PARAMETERS;

U.S. patent application Ser. No. 17/957,933, titled ADAPTIVE FIRING CONTROL ALGORITHM BASED ON MECHANICAL ACTUATION OF USER CONTROLS;

U.S. patent application Ser. No. 17/957,933, titled ADAPTATION OF INDEPENDENT FIRING AND CLOSURE POWERED STAPLING SYSTEMS;

U.S. patent application Ser. No. 17/957,954, titled MONITORING ONE DRIVE SYSTEM TO ADAPT THE MOTOR DRIVEN ASPECT OF A SECOND DRIVE SYSTEM;

U.S. patent application Ser. No. 17/957,975, titled ADJUSTMENT OF THE MOTOR CONTROL PROGRAM BASED ON DETECTION OF INDIVIDUAL DEVICE DRIVE TRAIN PROPERTIES;

U.S. patent application Ser. No. 17/957,984, titled ADJUSTMENT OF A MOTOR CONTROL COMMAND SIGNAL TO ADAPT TO SYSTEM CHANGES;

U.S. patent application Ser. No. 17/957,995, titled SURGICAL SYSTEMS WITH SYNCHRONIZED DISTRIBUTED PROCESSING CAPABILITIES;

U.S. patent application Ser. No. 17/958,001 titled SURGICAL SYSTEM WITH MOTOR RELATIVE CAPACITY INTERROGATIONS;

U.S. patent application Ser. No. 17/958,008, titled MOTOR CONTROL OF SURGICAL INSTRUMENT SYSTEMS;

U.S. patent application Ser. No. 17/958,013, titled SURGICAL SYSTEM WITH AMPLITUDE AND PULSE WIDTH MODULATION ADJUSTMENTS;

U.S. patent application Ser. No. 17/958,024, titled SURGICAL ALGORITHMS WITH INCREMENTAL SENSORY ACTIONS;

U.S. patent application Ser. No. 17/958,028, titled UTILIZING LOCAL FIRING PARAMETERS TO INITIATE MOTOR CONTROL ADJUSTMENTS IN SURGICAL SYSTEMS;

U.S. patent application Ser. No. 17/958,037, titled SURGICAL SYSTEMS WITH DYNAMIC FORCE TO FIRE ADJUSTMENTS; published as U.S. Pat. No. 11,931,037 on Mar. 19, 2024.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

Figure 2:
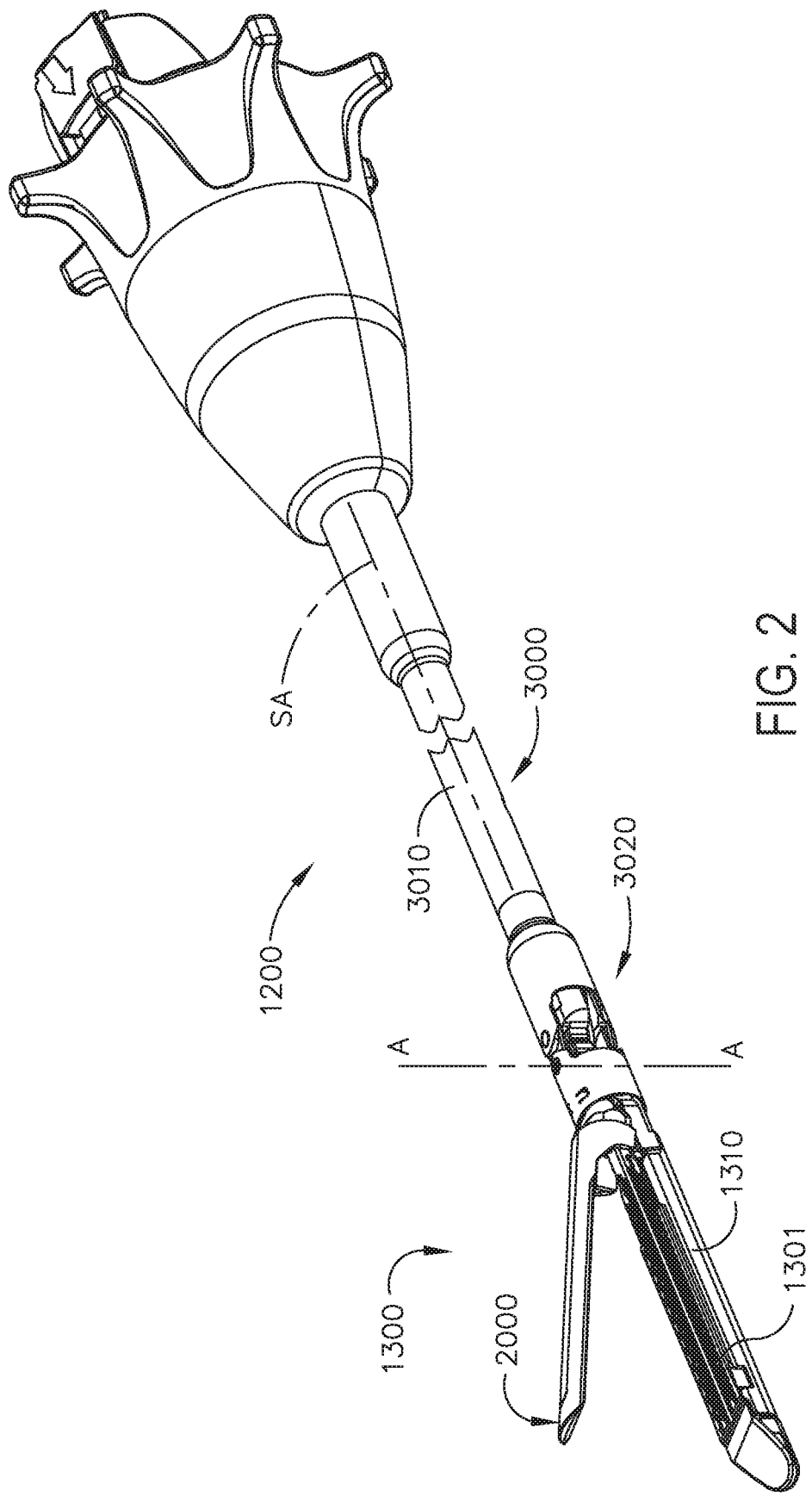
FIG. 2 is a perspective view of an interchangeable surgical shaft assembly of the powered surgical stapling system of FIG. 1.
Figure 3:
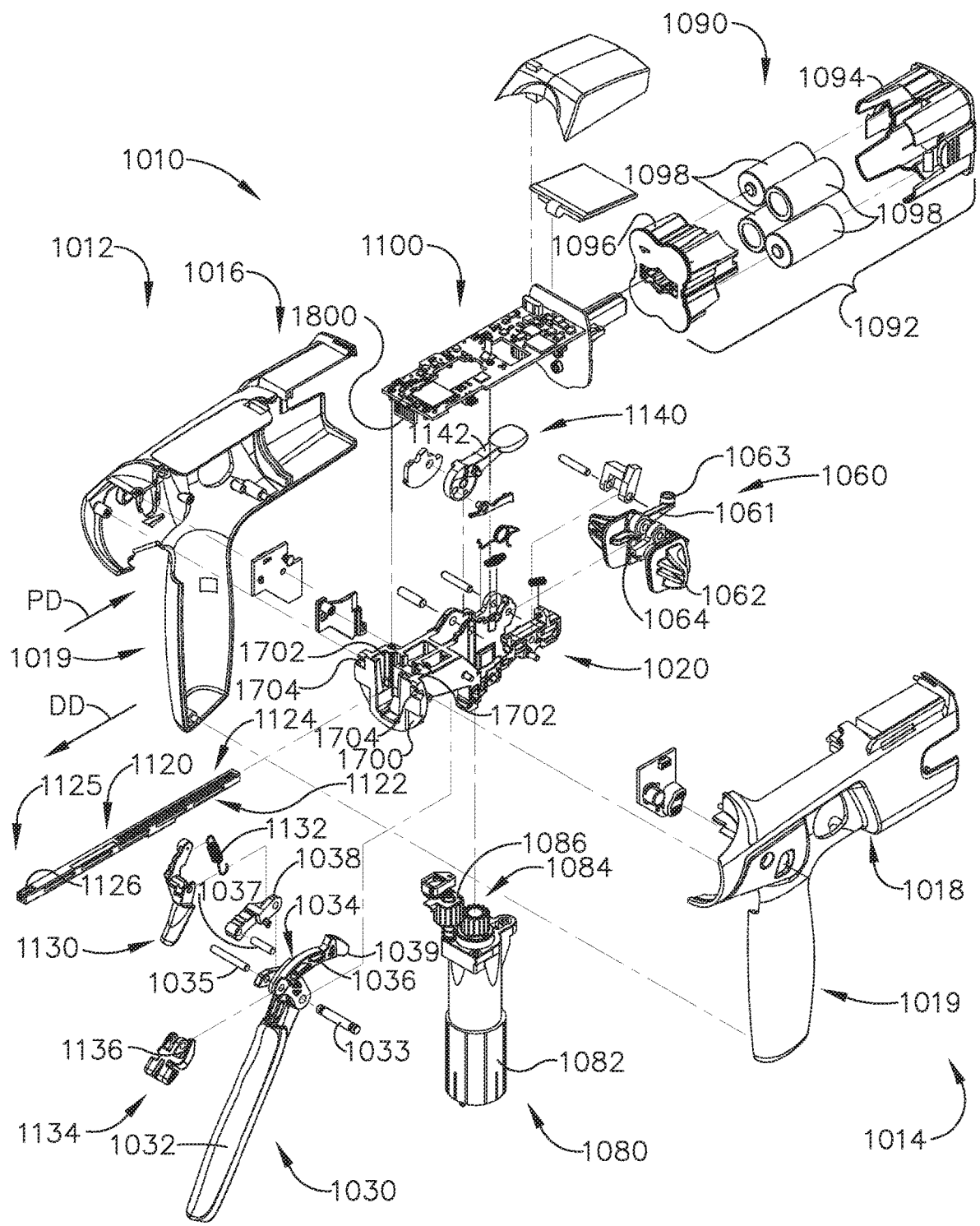
FIG. 3 is an exploded assembly view of portions of a handle assembly of the powered surgical stapling system of FIG. 1.

FIG. 1 illustrates the surgical instrument 1010 that includes an interchangeable shaft assembly 1200 operably coupled to a housing 1012. FIG. 2 illustrates the interchangeable shaft assembly 1200 detached from the housing 1012 or handle 1014. As can be seen in FIG. 3, the handle 1014 may comprise a pair of interconnectable handle housing segments 1016 and 1018 that may be interconnected by screws, snap features, adhesive, etc. In the illustrated arrangement, the handle housing segments 1016, 1018 cooperate to form a pistol grip portion 1019. FIGS. 1 and 3 depict a motor-driven surgical cutting and fastening instrument 1010 that may or may not be reused. In the illustrated embodiment, the instrument 1010 includes a proximal housing 1012 that comprises a handle 1014 that is configured to be grasped, manipulated and actuated by the clinician. The housing 1012 is configured for operable attachment to an interchangeable shaft assembly 1200 that has a surgical end effector 1300 operably coupled thereto that is configured to perform one or more surgical tasks or procedures. As the present Detailed Description proceeds, it will be understood that the various forms of interchangeable shaft assemblies disclosed herein may also be effectively employed in connection with robotically-controlled surgical systems. Thus, the term "housing" may also encompass a housing or similar portion of a robotic system that houses or otherwise operably supports at least one drive system that is configured to generate and apply at least one control motion which could be used to actuate the interchangeable shaft assemblies disclosed herein and their respective equivalents. In addition, various components may be "housed" or contained in the housing or various components may be "associated with" a housing. In such instances, the components may not be contained within the housing or supported directly by the housing. The term "frame" may refer to a portion of a handheld surgical instrument. The term "frame" may also represent a portion of a robotically controlled surgical instrument and/or a portion of the robotic system that may be used to operably control a surgical instrument. For example, the interchangeable shaft assemblies disclosed herein may be employed with various robotic systems, instruments, components and methods disclosed in U.S. Pat. No. 9,072,535, entitled SURGICAL STAPLING INSTRUMENTS WITH ROTATABLE STAPLE DEPLOYMENT ARRANGEMENTS, which is incorporated by reference herein in its entirety.

The proximal housing 1012 depicted in FIG. 1 is shown in connection with an interchangeable shaft assembly 1200 (FIGS. 2, 4 and 5) that includes an end effector 1300 that comprises a surgical cutting and fastening device that is configured to operably support a surgical staple cartridge 1301 therein. The housing 1012 may be configured for use in connection with interchangeable shaft assemblies that include end effectors that are adapted to support different sizes and types of staple cartridges, have different shaft lengths, sizes, and types, etc. In addition, the housing 1012 may also be effectively employed with a variety of other interchangeable shaft assemblies including those assemblies that are configured to apply other motions and forms of energy such as, for example, radio frequency (RF) energy, ultrasonic energy and/or motion to end effector arrangements adapted for use in connection with various surgical applications and procedures. Furthermore, the end effectors, shaft assemblies, handles, surgical instruments, and/or surgical instrument systems can utilize any suitable fastener that can be gripped and manipulated by the clinician. As will be discussed in further detail below, the handle 1014 operably supports a plurality of drive systems therein that are configured to generate and apply various control motions to corresponding portions of the interchangeable shaft assembly that is operably attached thereto.

Referring now to FIG. 3, the handle 1014 may further include a frame 1020 that operably supports a plurality of drive systems. For example, the frame 1020 can operably support a "first" or closure drive system, generally designated as 1030, which may be employed to apply closing and opening motions to the interchangeable shaft assembly 1200 that is operably attached or coupled thereto. In at least one form, the closure drive system 1030 may include an actuator in the form of a closure trigger 1032 that is pivotally supported by the frame 1020. More specifically, as illustrated in FIG. 3, the closure trigger 1032 is pivotally coupled to the handle 1014 by a pin 1033. Such arrangement enables the closure trigger 1032 to be manipulated by a clinician such that when the clinician grips the pistol grip portion 1019 of the handle 1014, the closure trigger 1032 may be easily pivoted from a starting or "unactuated" position to an "actuated" position and more particularly to a fully compressed or fully actuated position. The closure trigger 1032 may be biased into the unactuated position by spring or other biasing arrangement (not shown). In various forms, the closure drive system 1030 further includes a closure linkage assembly 1034 that is pivotally coupled to the closure trigger 1032. As can be seen in FIG. 3, the closure linkage assembly 1034 may include a first closure link 1036 and a second closure link 1038 that are pivotally coupled to the closure trigger 1032 by a pin 1035. The second closure link 1038 may also be referred to herein as an "attachment member" and include a transverse attachment pin 1037.

Still referring to FIG. 3, it can be observed that the first closure link 1036 may have a locking wall or end 1039 thereon that is configured to cooperate with a closure release assembly 1060 that is pivotally coupled to the frame 1020. In at least one form, the closure release assembly 1060 may comprise a release button assembly 1062 that has a distally protruding locking pawl 1064 formed thereon. The release button assembly 1062 may be pivoted in a counterclockwise direction by a release spring (not shown). As the clinician depresses the closure trigger 1032 from its unactuated position towards the pistol grip portion 1019 of the handle 1014, the first closure link 1036 pivots upward to a point wherein the locking pawl 1064 drops into retaining engagement with the locking wall 1039 on the first closure link 1036 thereby preventing the closure trigger 1032 from returning to the unactuated position. Thus, the closure release assembly 1060 serves to lock the closure trigger 1032 in the fully actuated position. When the clinician desires to unlock the closure trigger 1032 to permit it to be biased to the unactuated position, the clinician simply pivots the closure release button assembly 1062 such that the locking pawl 1064 is moved out of engagement with the locking wall 1039 on the first closure link 1036. When the locking pawl 1064 has been moved out of engagement with the first closure link 1036, the closure trigger 1032 may pivot back to the unactuated position. Other closure trigger locking and release arrangements may also be employed.

An arm 1061 may extend from the closure release button assembly 1062. A magnetic element 1063, such as a permanent magnet, for example, may be mounted to the arm 1061. When the closure release button assembly 1062 is rotated from its first position to its second position, the magnetic element 1063 can move toward a circuit board 1100. The circuit board 1100 can include at least one sensor that is configured to detect the movement of the magnetic element 1063. In at least one embodiment, for example, a "Hall Effect" sensor (not shown) can be mounted to the bottom surface of the circuit board 1100. The Hall Effect sensor can be configured to detect changes in a magnetic field surrounding the Hall Effect sensor caused by the movement of the magnetic element 1063. The Hall Effect sensor can be in signal communication with a microcontroller, for example, which can determine whether the closure release button assembly 1062 is in its first position, which is associated with the unactuated position of the closure trigger 1032 and the open configuration of the end effector, its second position, which is associated with the actuated position of the closure trigger 1032 and the closed configuration of the end effector, and/or any position between the first position and the second position.

In at least one form, the handle 1014 and the frame 1020 may operably support another drive system referred to herein as a firing drive system 1080 that is configured to apply firing motions to corresponding portions of the interchangeable shaft assembly attached thereto. The firing drive system 1080 may also be referred to herein as a "second drive system". The firing drive system 1080 may employ an electric motor 1082 that is located in the pistol grip portion 1019 of the handle 1014. In various forms, the motor 1082 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. The motor 1082 may be powered by a power source 1090 that in one form may comprise a removable power pack 1092. As can be seen in FIG. 3, for example, the power pack 1092 may comprise a proximal housing portion 1094 that is configured for attachment to a distal housing portion 1096. The proximal housing portion 1094 and the distal housing portion 1096 are configured to operably support a plurality of batteries 1098 therein. Batteries 1098 may each comprise, for example, a Lithium Ion ("LI") or other suitable battery. The distal housing portion 1096 is configured for removable operable attachment to the circuit board 1100 which is also operably coupled to the motor 1082. A number of batteries 1098 may be connected in series may be used as the power source for the surgical instrument 1010. In addition, the power source 1090 may be replaceable and/or rechargeable.

As outlined above with respect to other various forms, the electric motor 1082 can include a rotatable shaft (not shown) that operably interfaces with a gear reducer assembly 1084 that is mounted in meshing engagement with a with a set, or rack, of drive teeth 1122 on a longitudinally movable drive member 1120. In use, a voltage polarity provided by the power source 1090 can operate the electric motor 1082 in a clockwise direction wherein the voltage polarity applied to the electric motor by the battery can be reversed in order to operate the electric motor 1082 in a counter-clockwise direction. When the electric motor 1082 is rotated in one direction, the drive member 1120 will be axially driven in the distal direction "DD". When the motor 1082 is driven in the opposite rotary direction, the drive member 1120 will be axially driven in a proximal direction "PD". The handle 1014 can include a switch which can be configured to reverse the polarity applied to the electric motor 1082 by the power source 1090. As with the other forms described herein, the handle 1014 can also include a sensor that is configured to detect the position of the drive member 1120 and/or the direction in which the drive member 1120 is being moved.

Actuation of the motor 1082 can be controlled by a firing trigger 1130 that is pivotally supported on the handle 1014. The firing trigger 1130 may be pivoted between an unactuated position and an actuated position. The firing trigger 1130 may be biased into the unactuated position by a spring 1132 or other biasing arrangement such that when the clinician releases the firing trigger 1130, it may be pivoted or otherwise returned to the unactuated position by the spring 1132 or biasing arrangement. In at least one form, the firing trigger 1130 can be positioned "outboard" of the closure trigger 1032 as was discussed above. In at least one form, a firing trigger safety button 1134 may be pivotally mounted to the closure trigger 1032 by the pin 1035. The safety button 1134 may be positioned between the firing trigger 1130 and the closure trigger 1032 and have a pivot arm 1136 protruding therefrom. When the closure trigger 1032 is in the unactuated position, the safety button 1134 is contained in the handle 1014 where the clinician cannot readily access it and move it between a safety position preventing actuation of the firing trigger 1130 and a firing position wherein the firing trigger 1130 may be fired. As the clinician depresses the closure trigger 1032, the safety button 1134 and the firing trigger 1130 pivot down wherein they can then be manipulated by the clinician.

As indicated above, in at least one form, the longitudinally movable drive member 1120 has a rack of teeth 1122 formed thereon for meshing engagement with a corresponding drive gear 1086 of the gear reducer assembly 1084. At least one form also includes a manually-actuatable "bailout" assembly 1140 that is configured to enable the clinician to manually retract the longitudinally movable drive member 1120 should the motor 1082 become disabled. The bailout assembly 1140 may include a lever or bailout handle assembly 1142 that is configured to be manually pivoted into ratcheting engagement with teeth 1124 also provided in the drive member 1120. Thus, the clinician can manually retract the drive member 1120 by using the bailout handle assembly 1142 to ratchet the drive member 1120 in the proximal direction "PD". U.S. Pat. No. 8,608,045, entitled POWERED SURGICAL CUTTING AND STAPLING APPARATUS WITH MANUALLY RETRACTABLE FIRING SYSTEM, discloses bailout arrangements and other components, arrangements and systems that may also be employed with the various instruments disclosed herein. U.S. Pat. No. 8,608,045, is hereby incorporated by reference herein in its entirety.

Figure 4:
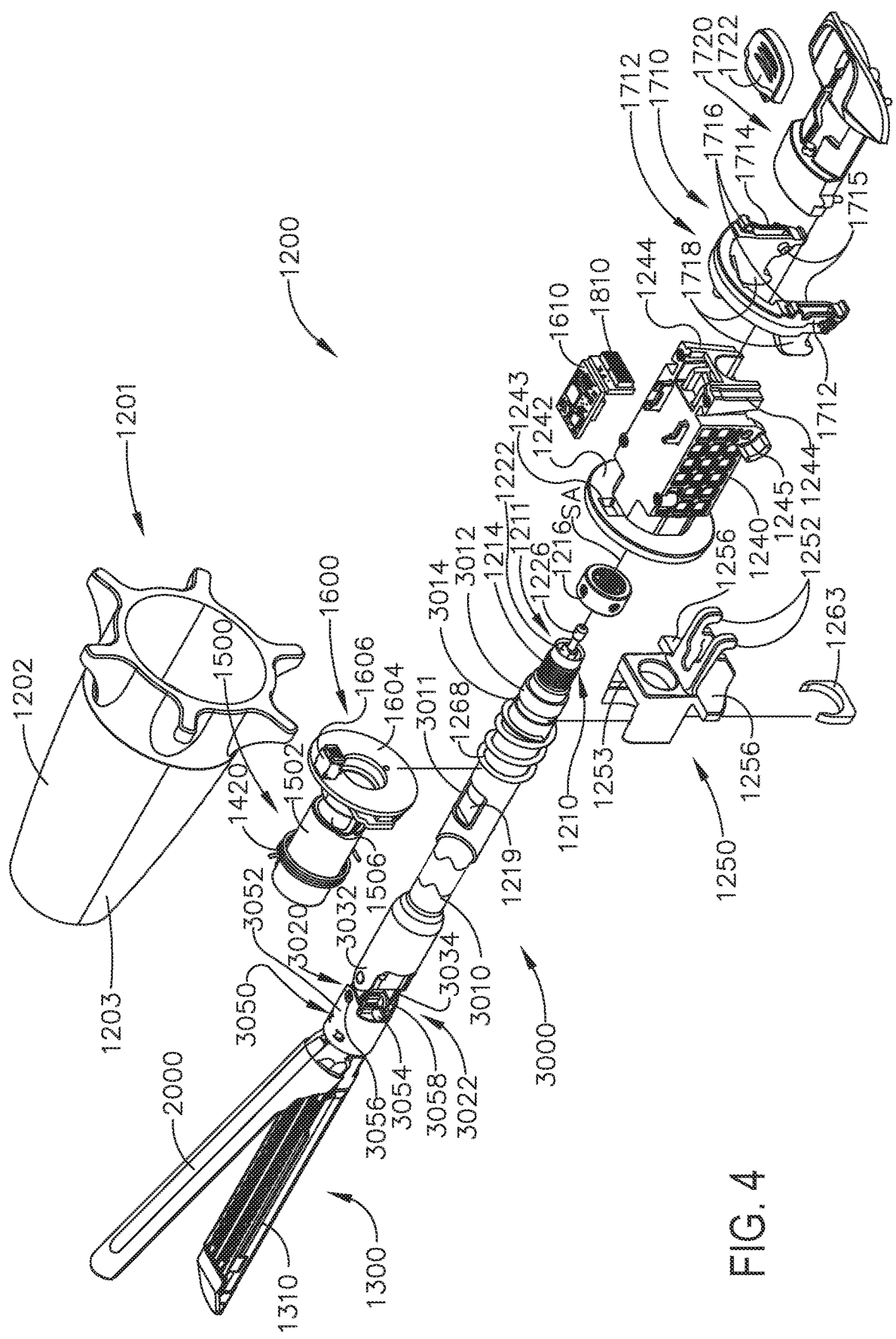
FIG. 4 is an exploded assembly view of the interchangeable surgical shaft assembly of FIG. 2.
Figure 5:
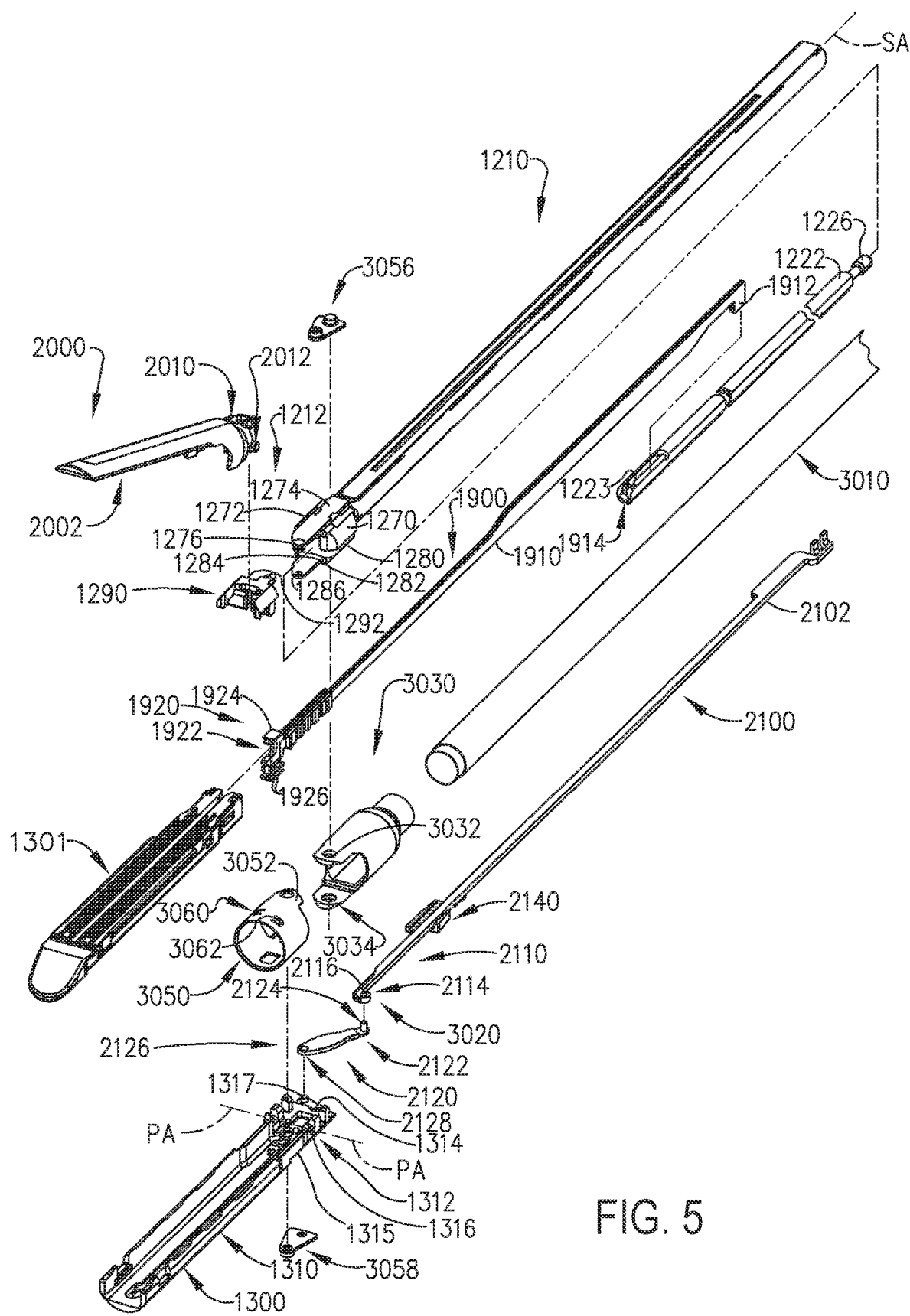
FIG. 5 is another partial exploded assembly view of a portion of the interchangeable surgical shaft assembly of FIG. 4.

Turning now to FIGS. 2 and 5, the interchangeable shaft assembly 1200 includes a surgical end effector 1300 that comprises an elongate channel 1310 that is configured to operably support a staple cartridge 1301 therein. The end effector 1300 may further include an anvil 2000 that is pivotally supported relative to the elongate channel 1310. The interchangeable shaft assembly 1200 may further include an articulation joint 3020 and an articulation lock 2140 which can be configured to releasably hold the end effector 1300 in a desired position relative to a shaft axis SA. Examples of various features of at least one form of the end effector 1300, the articulation joint 3020 and articulation locks may be found in U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541. The entire disclosure of U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541, is hereby incorporated by reference herein. As can be seen in FIG. 4, the interchangeable shaft assembly 1200 can further include a proximal housing or nozzle 1201 comprised of nozzle portions 1202 and 1203.

The interchangeable shaft assembly 1200 can further include a closure system or closure member assembly 3000 which can be utilized to close and/or open the anvil 2000 of the end effector 1300. The shaft assembly 1200 can include a spine 1210 that is configured to, one, slidably support a firing member therein and, two, slidably support the closure member assembly 3000 which extends around the spine 1210. As can be seen in FIG. 5, a distal end 1212 of spine 1210 terminates in an upper lug mount feature 1270 and in a lower lug mount feature 1280. The upper lug mount feature 1270 is formed with a lug slot 1272 therein that is adapted to mountingly support an upper mounting link 1274 therein. Similarly, the lower lug mount feature 1280 is formed with a lug slot 1282 therein that is adapted to mountingly support a lower mounting link 1284 therein. The upper mounting link 1274 includes a pivot socket 1276 therein that is adapted to rotatably receive therein a pivot pin 1292 that is formed on a channel cap or anvil retainer 1290 that is attached to a proximal end portion 1312 of the elongate channel 1310. The lower mounting link 1284 includes lower pivot pin 1286 that adapted to be received within a pivot hole 1314 formed in the proximal end portion 1312 of the elongate channel 1310. See FIG. 5. The lower pivot pin 1286 is vertically aligned with the pivot socket 1276 to define an articulation axis AA about which the surgical end effector 1300 may articulate relative to the shaft axis SA. See FIG. 2.

In the illustrated example, the surgical end effector 1300 is selectively articulatable about the articulation axis AA by an articulation system 2100. In one form, the articulation system 2100 includes proximal articulation driver 2102 that is pivotally coupled to an articulation link 2120. As can be most particularly seen in FIG. 5, an offset attachment lug 2114 is formed on a distal end 2110 of the proximal articulation driver 2102. A pivot hole 2116 is formed in the offset attachment lug 2114 and is configured to pivotally receive therein a proximal link pin 2124 formed on the proximal end 2122 of the articulation link 2120. A distal end 2126 of the articulation link 2120 includes a pivot hole 2128 that is configured to pivotally receive therein a channel pin 1317 formed on the proximal end portion 1312 of the elongate channel 1310. Thus, axial movement of proximal articulation driver 2102 will thereby apply articulation motions to the elongate channel 1310 to thereby cause the surgical end effector 1300 to articulate about the articulation axis AA relative to the spine 1210. Further details concerning the construction and operation of the articulation system 2100 may be found in various references incorporated by reference herein including U.S. patent application Ser. No. 15/635,631, filed Jun. 28, 2017, entitled SURGICAL INSTRUMENT WITH AXIALLY MOVABLE CLOSURE MEMBER, now U.S. Patent Application Publication No. 2019/0000464, the entire disclosure of which is hereby incorporated by reference herein. In various circumstances, the proximal articulation driver 2102 can be held in position by an articulation lock 2140 when the proximal articulation driver 2102 is not being moved in the proximal or distal directions. Additional details regarding an example of an articulation lock 2140 may be found in U.S. patent application Ser. No. 15/635,631, now U.S. Patent Application Publication No. 2019/0000464, as well as in other references incorporated by reference herein.

In various circumstances, the spine 1210 can comprise a proximal end 1211 which is rotatably supported in a chassis 1240. In one arrangement, for example, the proximal end 1211 of the spine 1210 has a thread 1214 formed thereon for threaded attachment to a spine bearing 1216 configured to be supported within the chassis 1240. See FIG. 4. Such an arrangement facilitates rotatable attachment of the spine 1210 to the chassis 1240 such that the spine 1210 may be selectively rotated about a shaft axis SA relative to the chassis 1240.

Referring primarily to FIG. 4, the interchangeable shaft assembly 1200 includes a closure shuttle 1250 that is slidably supported within the chassis 1240 such that it may be axially moved relative thereto. The closure shuttle 1250 includes a pair of proximally-protruding hooks 1252 that are configured for attachment to the attachment pin 1037 (FIG. 3) that is attached to the second closure link 1038 as will be discussed in further detail below. In at least one example, the closure member assembly 3000 comprises a proximal closure member segment 3010 that has a proximal end 3012 that is coupled to the closure shuttle 1250 for relative rotation thereto. For example, a U shaped connector 1263 is inserted into an annular slot 3014 in the proximal end 3012 of the proximal closure member segment 3010 and is retained within vertical slots 1253 in the closure shuttle 1250. Such an arrangement serves to attach the proximal closure member segment 3010 to the closure shuttle 1250 for axial travel therewith while enabling the proximal closure member segment 3010 to rotate relative to the closure shuttle 1250 about the shaft axis SA. A closure spring 1268 is journaled on the proximal closure member segment 3010 and serves to bias the proximal closure member segment 3010 in the proximal direction "PD" which can serve to pivot the closure trigger 1032 into the unactuated position when the shaft assembly is operably coupled to the handle 1014.

In at least one form, the interchangeable shaft assembly 1200 may further include an articulation joint 3020. Other interchangeable shaft assemblies, however, may not be capable of articulation. As can be seen in FIG. 5, for example, a distal closure member or distal closure tube segment 3030 is coupled to the distal end of the proximal closure member segment 3010. The articulation joint 3020 includes a double pivot closure sleeve assembly 3022. According to various forms, the double pivot closure sleeve assembly 3022 includes an end effector closure tube 3050 having upper and lower distally projecting tangs 3052, 3054. An upper double pivot link 3056 includes upwardly projecting distal and proximal pivot pins that engage respectively an upper distal pin hole in the upper proximally projecting tang 3052 and an upper proximal pin hole in an upper distally projecting tang 3032 on the distal closure tube segment 3030. A lower double pivot link 3058 includes upwardly projecting distal and proximal pivot pins that engage respectively a lower distal pin hole in the lower proximally projecting tang 3054 and a lower proximal pin hole in the lower distally projecting tang 3034. See FIGS. 4 and 5. As will be discussed in further detail below, the closure member assembly 3000 is translated distally (direction "DD") to close the anvil 2000, for example, in response to the actuation of the closure trigger 1032. The anvil 2000 is opened by proximally translating the closure member assembly 3000 which causes the end effector closure sleeve to interact with the anvil 2000 and pivot it to an open position.

As was also indicated above, the interchangeable shaft assembly 1200 further includes a firing member 1900 that is supported for axial travel within the spine 1210. The firing member 1900 includes an intermediate firing shaft portion 1222 that is configured for attachment to a distal cutting portion or knife bar 1910. The intermediate firing shaft portion 1222 may include a longitudinal slot 1223 in the distal end thereof which can be configured to receive a tab 1912 on the proximal end of the distal knife bar 1910. The longitudinal slot 1223 and the proximal end tab 1912 can be sized and configured to permit relative movement therebetween and can comprise a slip joint 1914. The slip joint 1914 can permit the intermediate firing shaft portion 1222 of the firing member 1900 to be moved to articulate the end effector 1300 without moving, or at least substantially moving, the knife bar 1910. Once the end effector 1300 has been suitably oriented, the intermediate firing shaft portion 1222 can be advanced distally until a proximal sidewall of the longitudinal slot 1223 comes into contact with the tab 1912 in order to advance the knife bar 1910 and fire the staple cartridge 1301 positioned within the channel 1310. The knife bar 1910 includes a knife portion 1920 that includes a blade or tissue cutting edge 1922 and includes an upper anvil engagement tab 1924 and lower channel engagement tabs 1926. Various firing member configurations and operations are disclosed in various other references incorporated herein by reference.

Embodiments are also envisioned where, in lieu of a slip joint 1914, a shifter assembly can be used. Details of such a shifter assembly and corresponding components, assemblies, and systems can be found in U.S. patent application Ser. No. 15/635,521, entitled SURGICAL INSTRUMENT LOCKOUT ARRANGEMENT, which is incorporated by reference herein in its entirety.

As can be seen in FIG. 4, the shaft assembly 1200 further includes a switch drum 1500 that is rotatably received on proximal closure member segment 3010. The switch drum 1500 comprises a hollow shaft segment 1502 that has a shaft boss formed thereon for receiving an outwardly protruding actuation pin therein. In various circumstances, the actuation pin extends through a longitudinal slot provided in the lock sleeve to facilitate axial movement of the lock sleeve when it is engaged with the articulation driver. A rotary torsion spring 1420 is configured to engage the boss on the switch drum 1500 and a portion of the nozzle housing 1203 to apply a biasing force to the switch drum 1500. The switch drum 1500 can further comprise at least partially circumferential openings 1506 defined therein which can be configured to receive circumferential mounts extending from the nozzle portions 1202, 1203 and permit relative rotation, but not translation, between the switch drum 1500 and the nozzle 1201. The mounts also extend through openings 3011 in the proximal closure member segment 3010 to be seated in recesses 1219 in the spine 1210. Rotation of the switch drum 1500 about the shaft axis SA will ultimately result in the rotation of the actuation pin and the lock sleeve between its engaged and disengaged positions. In one arrangement, the rotation of the switch drum 1500 may be linked to the axial advancement of the closure tube or closure member. Thus, in essence, actuation of the closure system may operably engage and disengage the articulation drive system with the firing drive system in the various manners described in further detail in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, and U.S. Pat. No. 9,913,642, entitled SURGICAL INSTRUMENT COMPRISING A SENSOR SYSTEM, the entire disclosures of each being hereby incorporated by reference herein. For example, when the closure tube is in its proximal-most position corresponding to a "jaws open" position, the closure member segment 3010 will have positioned the switch drum 1500 so as to link the articulation system with the firing drive system. When, the closure tube has been moved to its distal position corresponding to a "jaws closed" position, the closure tube has rotated the switch drum 1500 to a position wherein the articulation system is delinked from the firing drive system.

As also illustrated in FIG. 4, the shaft assembly 1200 can comprise a slip ring assembly 1600 which can be configured to conduct electrical power to and/or from the end effector 1300 and/or communicate signals to and/or from the end effector 1300, for example. The slip ring assembly 1600 can comprise a proximal connector flange 1604 that is mounted to a chassis flange 1242 that extends from the chassis 1240 and a distal connector flange that is positioned within a slot defined in the shaft housings. The proximal connector flange 1604 can comprise a first face and the distal connector flange can comprise a second face which is positioned adjacent to and movable relative to the first face. The distal connector flange can rotate relative to the proximal connector flange 1604 about the shaft axis SA. The proximal connector flange 1604 can comprise a plurality of concentric, or at least substantially concentric, conductors defined in the first face thereof. A connector can be mounted on the proximal side of the connector flange and may have a plurality of contacts wherein each contact corresponds to and is in electrical contact with one of the conductors. Such an arrangement permits relative rotation between the proximal connector flange 1604 and the distal connector flange while maintaining electrical contact therebetween. The proximal connector flange 1604 can include an electrical connector 1606 which can place the conductors in signal communication with a shaft circuit board 1610 mounted to the shaft chassis 1240, for example. In at least one instance, a wiring harness comprising a plurality of conductors can extend between the electrical connector 1606 and the shaft circuit board 1610. The electrical connector 1606 may extend proximally through a connector opening 1243 defined in the chassis flange 1242. See FIG. 4. Further details regarding slip ring assembly 1600 may be found in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552, and U.S. Pat. No. 9,345,481, entitled STAPLE CARTRIDGE TISSUE THICKNESS SENSOR SYSTEM, for example. U.S. patent application Ser. No. 13/803,086, now U.S. Patent Application Publication No. 2014/0263541, U.S. patent application Ser. No. 13/800,067, now U.S. Patent Application Publication No. 2014/0263552, and U.S. Pat. No. 9,345,481 are each hereby incorporated by reference herein in their respective entireties.

As discussed above, the shaft assembly 1200 can include a proximal portion which is fixably mounted to the handle 1014 and a distal portion which is rotatable about a longitudinal axis. The rotatable distal shaft portion can be rotated relative to the proximal portion about the slip ring assembly 1600, as discussed above. The distal connector flange of the slip ring assembly 1600 can be positioned within the rotatable distal shaft portion. Moreover, further to the above, the switch drum 1500 can also be positioned within the rotatable distal shaft portion. When the rotatable distal shaft portion is rotated, the distal connector flange and the switch drum 1500 can be rotated synchronously with one another. In addition, the switch drum 1500 can be rotated between a first position and a second position relative to the distal connector flange. When the switch drum 1500 is in its first position, the articulation drive system may be operably disengaged from the firing drive system and, thus, the operation of the firing drive system may not articulate the end effector 1300 of the shaft assembly 1200. When the switch drum 1500 is in its second position, the articulation drive system may be operably engaged with the firing drive system and, thus, the operation of the firing drive system may articulate the end effector 1300 of the shaft assembly 1200. When the switch drum 1500 is moved between its first position and its second position, the switch drum 1500 is moved relative to the distal connector flange. In various instances, the shaft assembly 1200 can comprise at least one sensor configured to detect the position of the switch drum 1500.

Referring again to FIG. 4, the chassis 1240 includes at least one, and preferably two, tapered attachment portions 1244 formed thereon that are adapted to be received within corresponding dovetail slots 1702 formed within a distal attachment flange portion 1700 of the frame 1020. See FIG. 3. Each dovetail slot 1702 may be tapered or, stated another way, be somewhat V-shaped to seatingly receive the attachment portions 1244 therein. As can be further seen in FIG. 4, a shaft attachment lug 1226 is formed on the proximal end of the intermediate firing shaft portion 1222. As will be discussed in further detail below, when the interchangeable shaft assembly 1200 is coupled to the handle 1014, the shaft attachment lug 1226 is received in a firing shaft attachment cradle 1126 formed in a distal end 1125 of the longitudinal drive member 1120. See FIG. 3.

Various shaft assembly embodiments employ a latch system 1710 for removably coupling the shaft assembly 1200 to the housing 1012 and more specifically to the frame 1020. As can be seen in FIG. 4, for example, in at least one form, the latch system 1710 includes a lock member or lock yoke 1712 that is movably coupled to the chassis 1240. In the illustrated embodiment, for example, the lock yoke 1712 has a U-shape with two spaced downwardly extending legs 1714. The legs 1714 each have a pivot lug 1715 formed thereon that are adapted to be received in corresponding holes 1245 formed in the chassis 1240. Such arrangement facilitates pivotal attachment of the lock yoke 1712 to the chassis 1240. The lock yoke 1712 may include two proximally protruding lock lugs 1716 that are configured for releasable engagement with corresponding lock detents or grooves 1704 in the distal attachment flange portion 1700 of the frame 1020. See FIG. 3. In various forms, the lock yoke 1712 is biased in the proximal direction by spring or biasing member (not shown). Actuation of the lock yoke 1712 may be accomplished by a latch button 1722 that is slidably mounted on a latch actuator assembly 1720 that is mounted to the chassis 1240. The latch button 1722 may be biased in a proximal direction relative to the lock yoke 1712. As will be discussed in further detail below, the lock yoke 1712 may be moved to an unlocked position by biasing the latch button in the distal direction which also causes the lock yoke 1712 to pivot out of retaining engagement with the distal attachment flange portion 1700 of the frame 1020. When the lock yoke 1712 is in "retaining engagement" with the distal attachment flange portion 1700 of the frame 1020, the lock lugs 1716 are retainingly seated within the corresponding lock detents or grooves 1704 in the distal attachment flange portion 1700.

When employing an interchangeable shaft assembly that includes an end effector of the type described herein that is adapted to cut and fasten tissue, as well as other types of end effectors, it may be desirable to prevent inadvertent detachment of the interchangeable shaft assembly from the housing during actuation of the end effector. For example, in use the clinician may actuate the closure trigger 1032 to grasp and manipulate the target tissue into a desired position. Once the target tissue is positioned within the end effector 1300 in a desired orientation, the clinician may then fully actuate the closure trigger 1032 to close the anvil 2000 and clamp the target tissue in position for cutting and stapling. In that instance, the first drive system 1030 has been fully actuated. After the target tissue has been clamped in the end effector 1300, it may be desirable to prevent the inadvertent detachment of the shaft assembly 1200 from the housing 1012. One form of the latch system 1710 is configured to prevent such inadvertent detachment.

As can be most particularly seen in FIG. 4, the lock yoke 1712 includes at least one and preferably two lock hooks 1718 that are adapted to contact corresponding lock lug portions 1256 that are formed on the closure shuttle 1250. When the closure shuttle 1250 is in an unactuated position (i.e., the first drive system 1030 is unactuated and the anvil 2000 is open), the lock yoke 1712 may be pivoted in a distal direction to unlock the interchangeable shaft assembly 1200 from the housing 1012. When in that position, the lock hooks 1718 do not contact the lock lug portions 1256 on the closure shuttle 1250. However, when the closure shuttle 1250 is moved to an actuated position (i.e., the first drive system 1030 is actuated and the anvil 2000 is in the closed position), the lock yoke 1712 is prevented from being pivoted to an unlocked position. Stated another way, if the clinician were to attempt to pivot the lock yoke 1712 to an unlocked position or, for example, the lock yoke 1712 was inadvertently bumped or contacted in a manner that might otherwise cause it to pivot distally, the lock hooks 1718 on the lock yoke 1712 will contact the lock lug portions 1256 on the closure shuttle 1250 and prevent movement of the lock yoke 1712 to an unlocked position.

Attachment of the interchangeable shaft assembly 1200 to the handle 1014 will now be described. To commence the coupling process, the clinician may position the chassis 1240 of the interchangeable shaft assembly 1200 above or adjacent to the distal attachment flange portion 1700 of the frame 1020 such that the tapered attachment portions 1244 formed on the chassis 1240 are aligned with the dovetail slots 1702 in the frame 1020. The clinician may then move the shaft assembly 1200 along an installation axis that is perpendicular to the shaft axis SA to seat the attachment portions 1244 in "operable engagement" with the corresponding dovetail slots 1702. In doing so, the shaft attachment lug 1226 on the intermediate firing shaft portion 1222 will also be seated in the cradle 1126 in the longitudinally movable drive member 1120 and the portions of the pin 1037 on the second closure link 1038 will be seated in the corresponding hooks 1252 in the closure shuttle 1250. As used herein, the term "operable engagement" in the context of two components means that the two components are sufficiently engaged with each other so that upon application of an actuation motion thereto, the components may carry out their intended action, function and/or procedure.

At least five systems of the interchangeable shaft assembly 1200 can be operably coupled with at least five corresponding systems of the handle 1014. A first system can comprise a frame system which couples and/or aligns the frame 1020 or spine 1210 of the shaft assembly 1200 with the frame 1020 of the handle 1014. Another system can comprise a closure drive system 1030 which can operably connect the closure trigger 1032 of the handle 1014 and a closure tube of the shaft assembly 1200. As outlined above, the closure shuttle 1250 of the shaft assembly 1200 can be engaged with the pin 1037 on the second closure link 1038. Another system can comprise the firing drive system 1080 which can operably connect the firing trigger 1130 of the handle 1014 with the intermediate firing shaft portion 1222 of the shaft assembly 1200. As outlined above, the shaft attachment lug 1226 can be operably connected with the cradle 1126 of the longitudinal drive member 1120. Another system can comprise an electrical system which can signal to a controller in the handle 1014, such as microcontroller, for example, that a shaft assembly, such as shaft assembly 1200, for example, has been operably engaged with the handle 1014 and/or, two, conduct power and/or communication signals between the shaft assembly 1200 and the handle 1014. For instance, the shaft assembly 1200 can include an electrical connector 1810 that is operably mounted to the shaft circuit board 1610. The electrical connector 1810 is configured for mating engagement with a corresponding electrical connector 1800 on the circuit board 1100. Further details regarding the circuitry and control systems may be found in U.S. patent application Ser. No. 13/803,086, now U.S. Patent Application Publication No. 2014/0263541 entitled ARTICULATABLE SURGICAL INSTRUMENT COMPRISING AN ARTICULATION LOCK, and U.S. patent application Ser. No. 14/226,142, now U.S. Pat. No. 9,913,642 entitled SURGICAL INSTRUMENT COMPRISING A SENSOR SYSTEM, the entire disclosures of each which were previously incorporated by reference herein. The fifth system may consist of the latching system for releasably locking the shaft assembly 1200 to the handle 1014.

The anvil 2000 in the illustrated example includes an anvil body 2002 that terminates in an anvil mounting portion 2010. The anvil mounting portion 2010 is movably or pivotably supported on the elongate channel 1310 for selective pivotal travel relative thereto about a fixed anvil pivot axis PA that is transverse to the shaft axis SA. In the illustrated arrangement, a pivot member or anvil trunnion 2012 extends laterally out of each lateral side of the anvil mounting portion 2010 to be received in a corresponding trunnion cradle 1316 formed in the upstanding walls 1315 of the proximal end portion 1312 of the elongate channel 1310. The anvil trunnions 2012 are pivotally retained in their corresponding trunnion cradle 1316 by the channel cap or anvil retainer 1290. The channel cap or anvil retainer 1290 includes a pair of attachment lugs that are configured to be retainingly received within corresponding lug grooves or notches formed in the upstanding walls 1315 of the proximal end portion 1312 of the elongate channel 1310. See FIG. 5.

Still referring to FIG. 5, in at least one arrangement, the distal closure member or end effector closure tube 3050 employs two axially offset, proximal and distal positive jaw opening features 3060 and 3062. The positive jaw opening features 3060, 3062 are configured to interact with corresponding relieved areas and stepped portions formed on the anvil mounting portion 2010 as described in further detail in U.S. patent application Ser. No. 15/635,631, entitled SURGICAL INSTRUMENT WITH AXIALLY MOVABLE CLOSURE MEMBER, now U.S. Patent Application Publication No. 2019/0000464, the entire disclosure which has been herein incorporated by reference. Other jaw opening arrangements may be employed.

Figure 6:
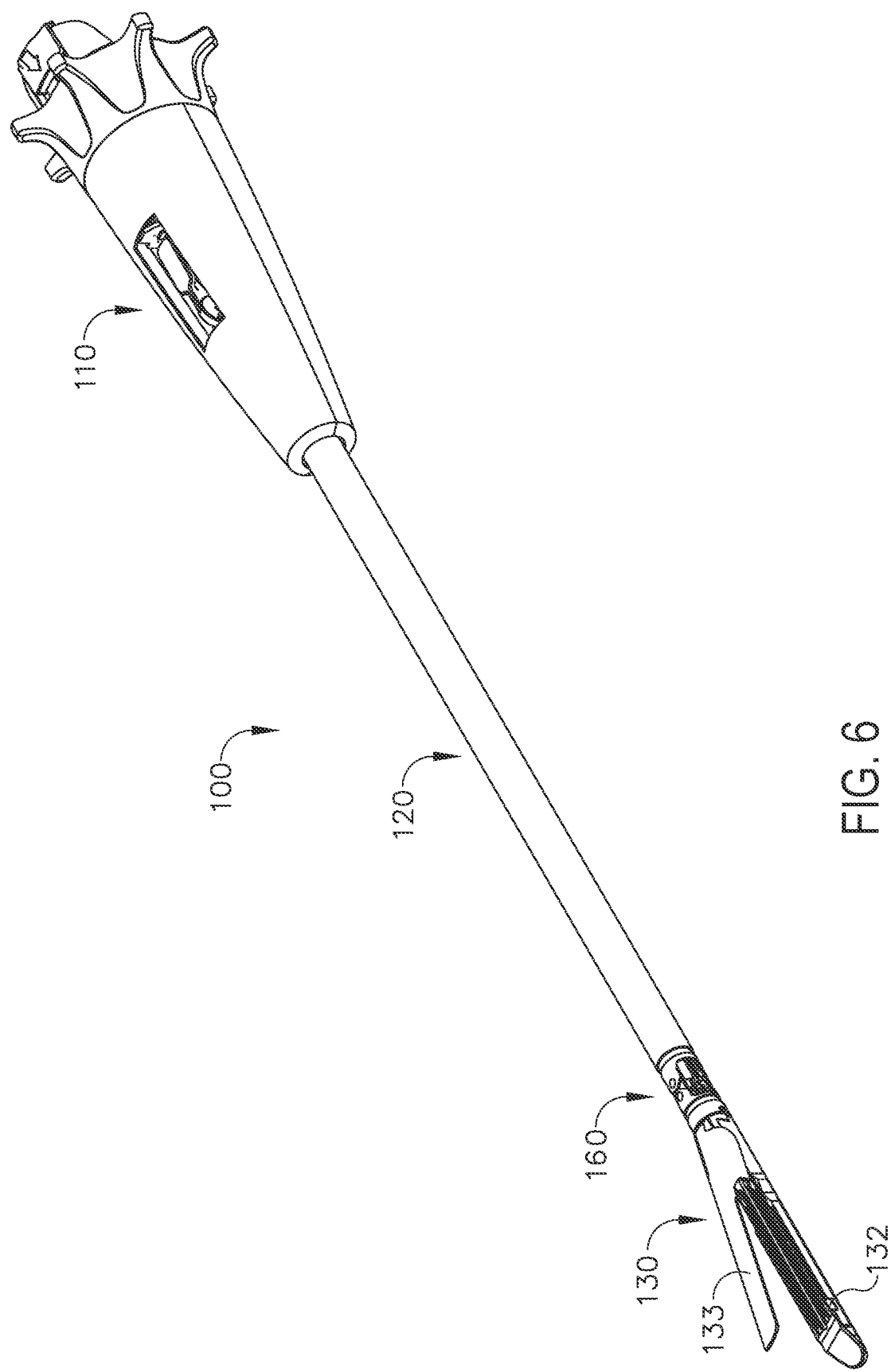
FIG. 6 is a perspective view of a shaft assembly in accordance with at least one embodiment.
Figure 7:
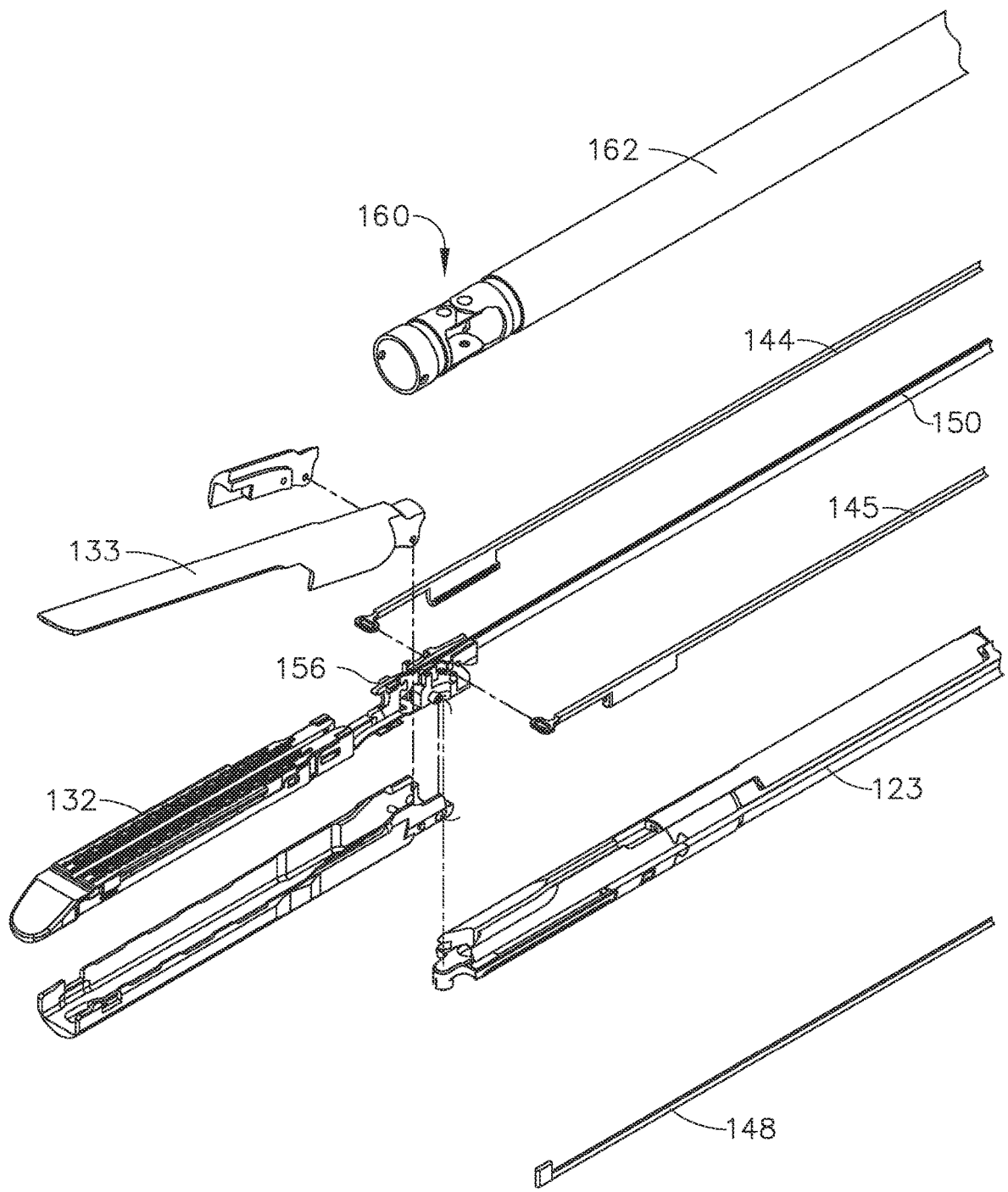
FIG. 7 is an exploded view of a distal end of the shaft assembly of FIG. 6.

A shaft assembly 100 is illustrated in FIGS. 6 and 7. The shaft assembly 100 comprises an attachment portion 110, a shaft 120 extending distally from the attachment portion 110, and an end effector 130 attached to the shaft 120. The shaft assembly 100 is configured to clamp, staple, and cut tissue. The attachment portion 110 is configured to be attached to a handle of a surgical instrument and/or the arm of a surgical robot, for example.

Referring to FIG. 7, the shaft assembly 100 comprises cooperating articulation rods 144, 145 configured to articulate the end effector 130 relative to the shaft 120 about an articulation joint 160. The shaft assembly 100 further comprises an articulation lock bar 148, an outer shaft tube 162, and a spine portion 123.

Referring to FIG. 7, the shaft assembly 100 comprises a firing shaft 150 including a firing member 156 attached to a distal end of the firing shaft 150. The firing member 156 comprises upper camming flanges configured to engage an anvil jaw 133 and lower camming members configured to engage a cartridge jaw 132. The firing shaft 150 is configured to be advanced distally through a closure stroke to clamp the anvil jaw 133 relative to the cartridge jaw 132 with the camming members. Further advancement of the firing shaft 150 through a firing stroke is configured to advance the firing member 156 through the cartridge jaw 132 to deploy staples from the cartridge jaw 132 and cut tissue during the firing stroke. More details of the shaft assembly 100 can be found in U.S. patent application Ser. No. 15/385,887 entitled METHOD FOR ATTACHING A SHAFT ASSEMBLY TO A SURGICAL INSTRUMENT AND, ALTERNATIVELY, TO A SURGICAL ROBOT, which is incorporated by reference in its entirety.

Figure 8:
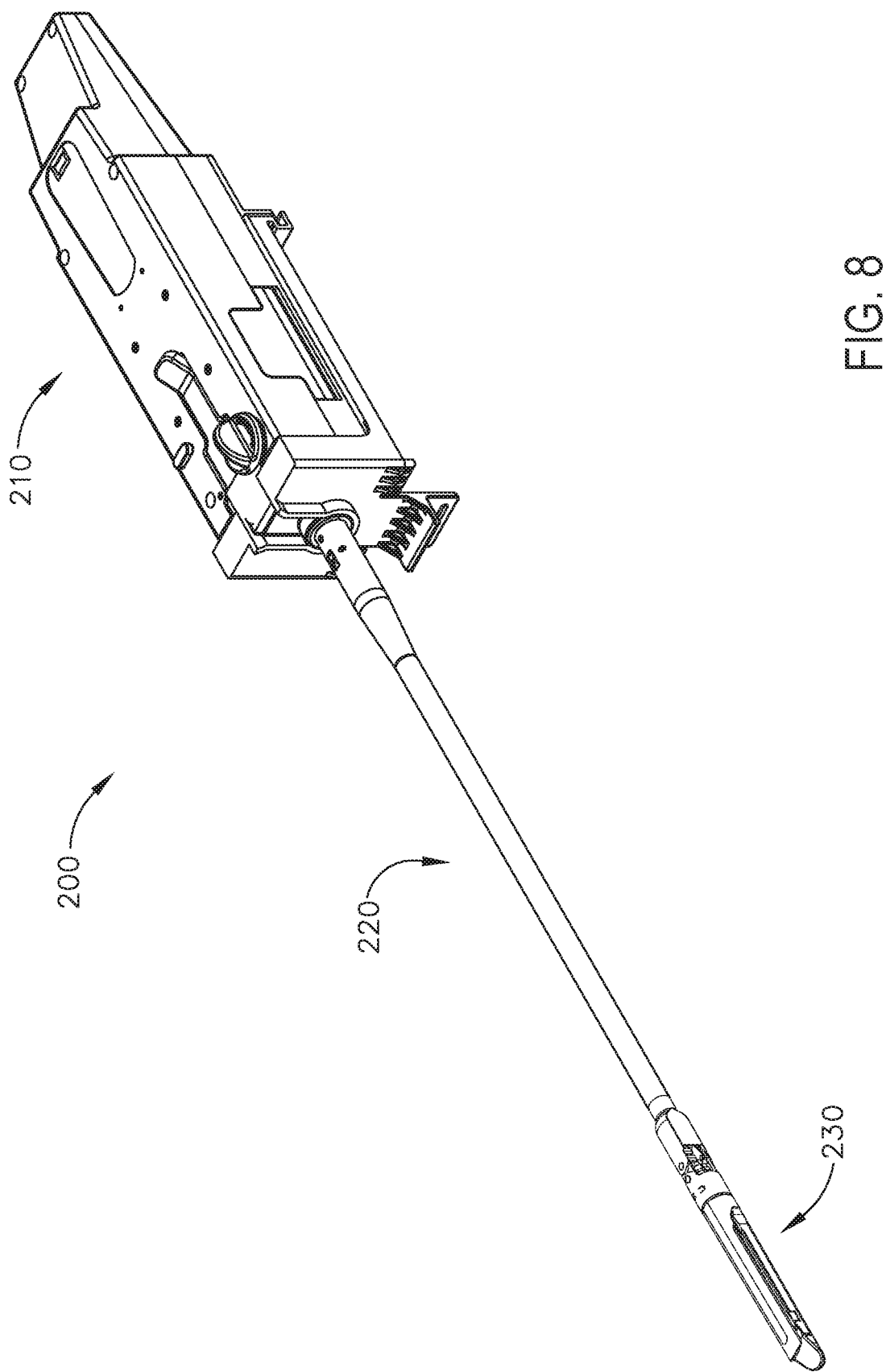
FIG. 8 is a perspective view of a surgical instrument assembly comprising a proximal control interface, a shaft assembly, and an end effector assembly.
Figure 9:
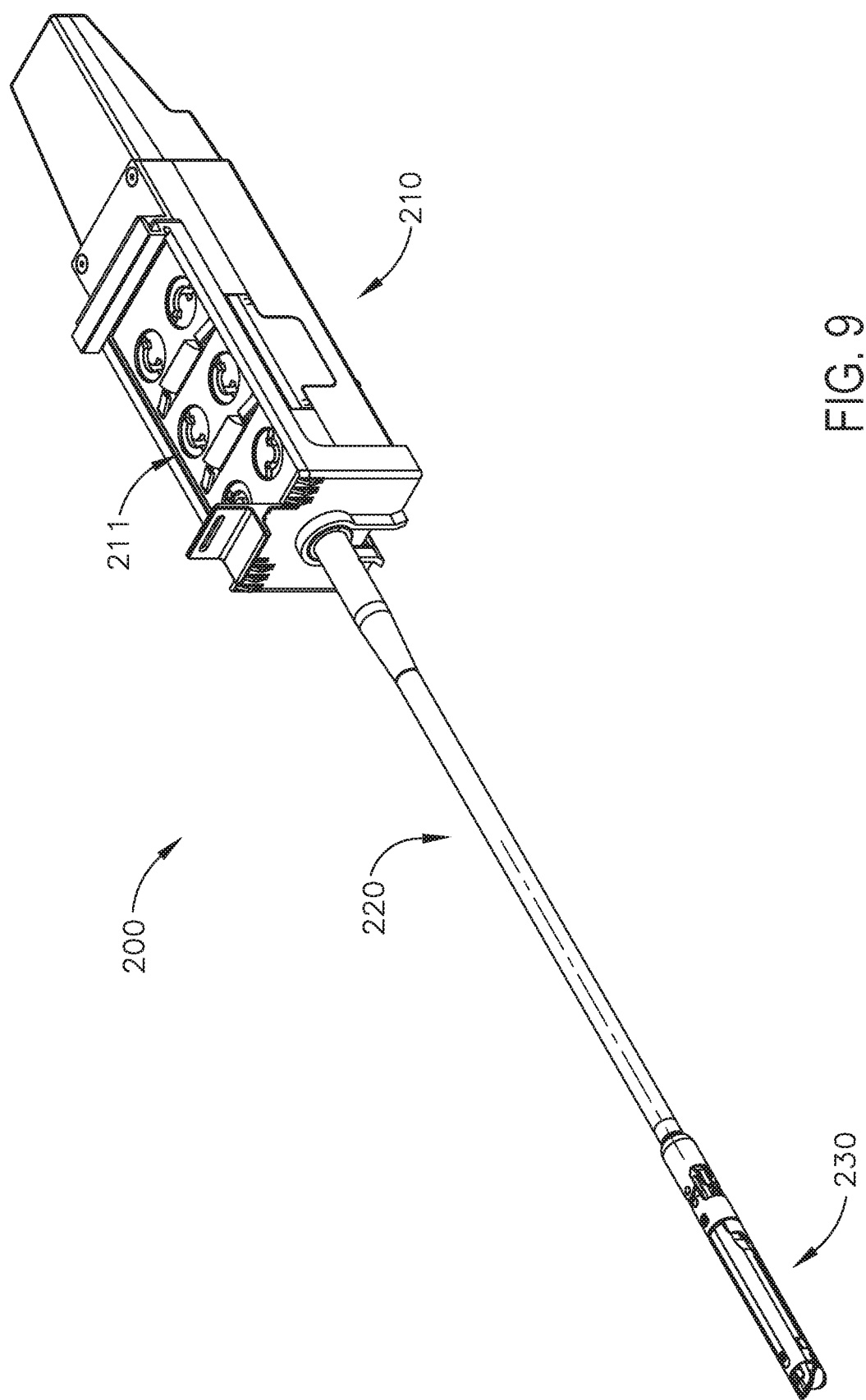
FIG. 9 is a bottom perspective view of the surgical instrument assembly of FIG. 8.

FIGS. 8 and 9 depict a surgical instrument assembly 200 configured to be used with a surgical robot. The surgical instrument assembly 200 is configured to staple and cut tissue, although the surgical instrument assembly 200 could be adapted to treat tissue in any suitable way, such as by applying heat energy, electrical energy, and/or vibrations to the tissue, for example. The surgical instrument assembly 200 comprises a proximal control interface 210 configured to be coupled to a robotic arm of a surgical robot and a shaft assembly 220 configured to be attached to the proximal control interface 210. The shaft assembly 220 comprises an end effector 230 configured to clamp, cut, and staple tissue. The proximal control interface 210 comprises a plurality of drive discs 211, each for actuating one or more functions of the surgical instrument assembly 200. Each drive disc 211 can be independently driven and/or cooperatively driven with one or more other drive discs 211 by one or more motors of the surgical robot and/or robotic arm of the surgical robot. More details about the surgical instrument assembly 200 can be found in U.S. patent application Ser. No. 15/847,297, entitled SURGICAL INSTRUMENTS WITH DUAL ARTICULATION DRIVERS, which is incorporated by reference in its entirety.

Figure 10:
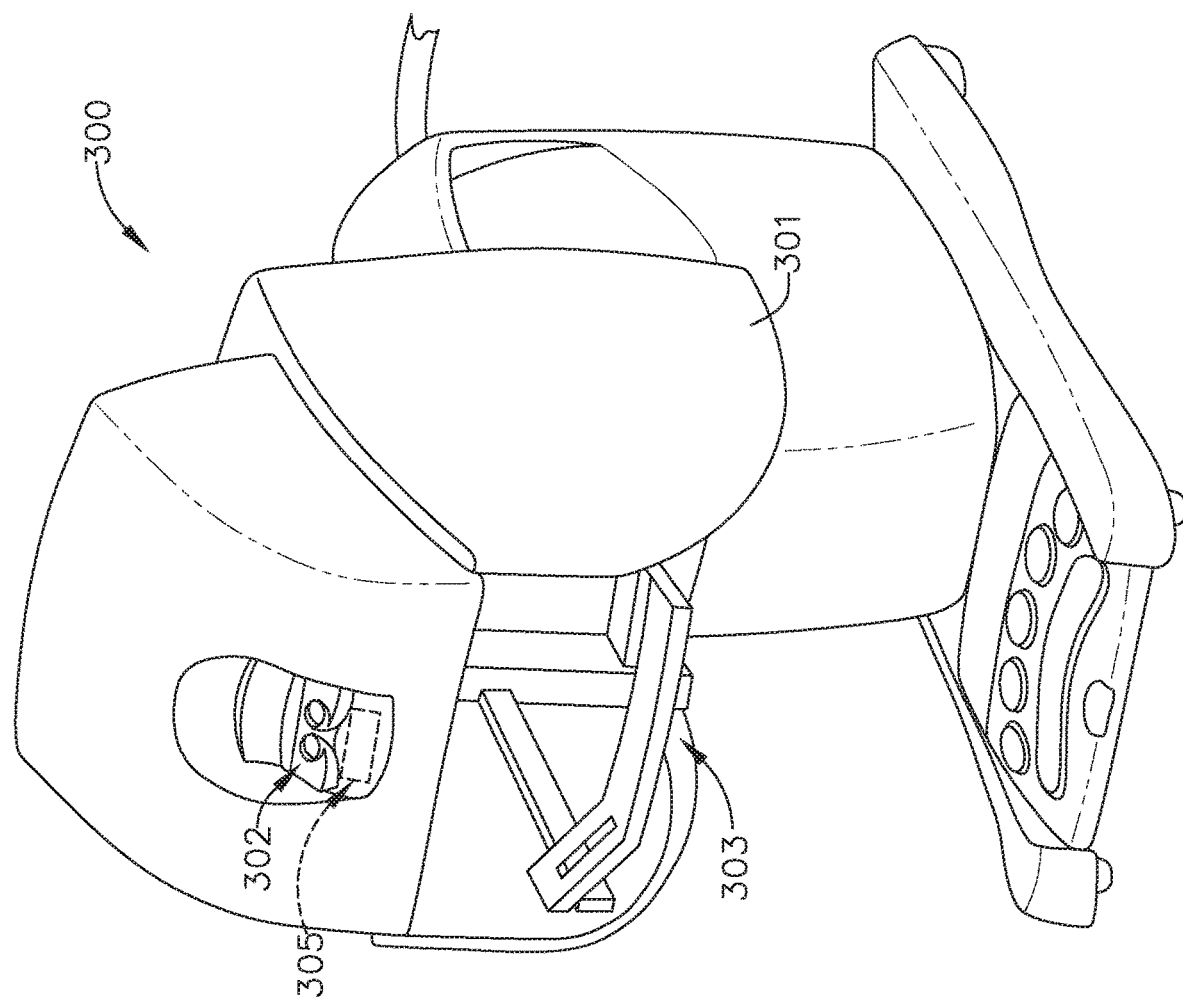
FIG. 10 is a perspective view of an example of one form of robotic controller according to one aspect of this disclosure.
Figure 11:
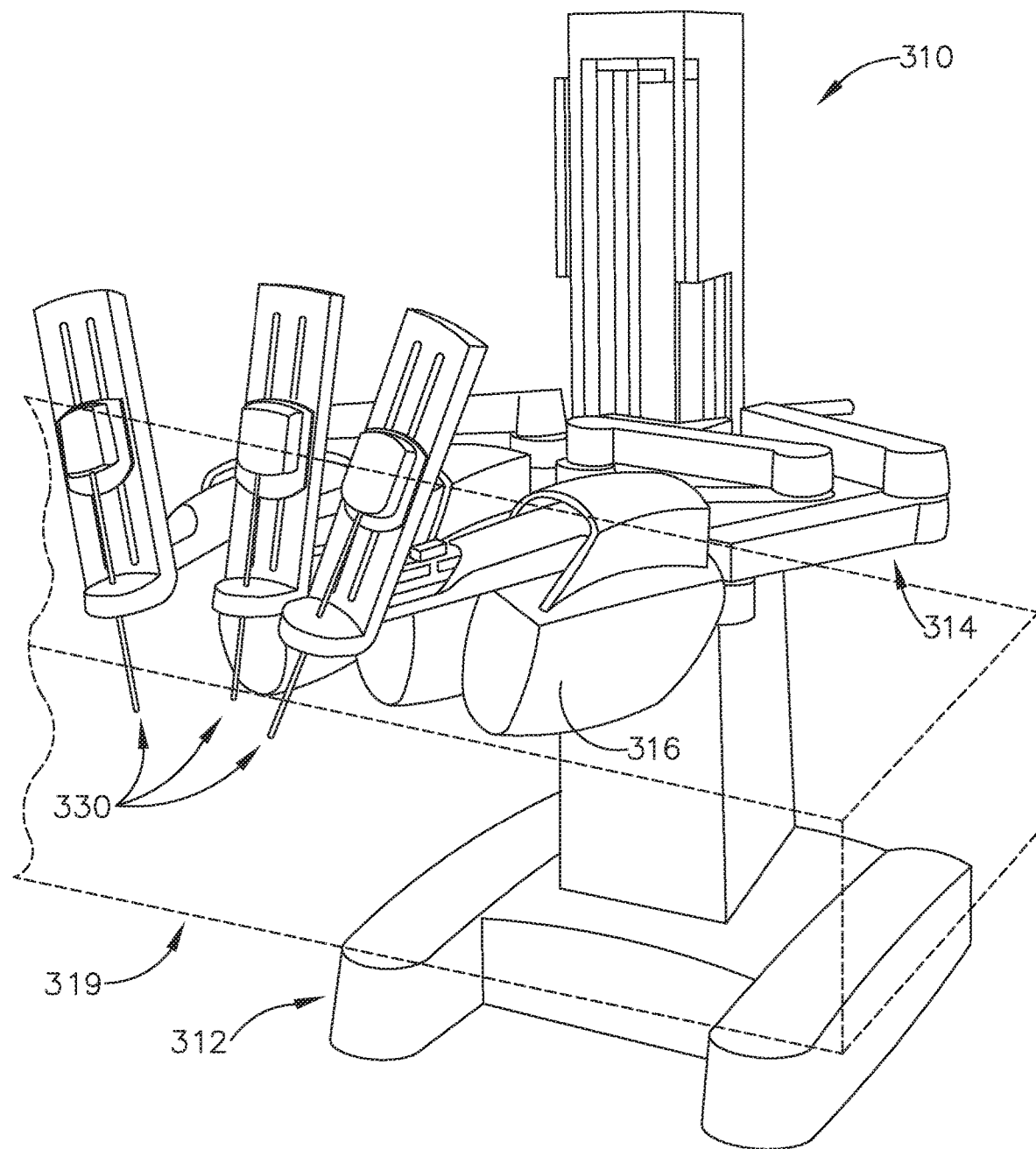
FIG. 11 is a perspective view of an example of one form of robotic surgical arm cart/manipulator of a robotic surgical system operably supporting a plurality of surgical tools according to one aspect of this disclosure.
Figure 12:
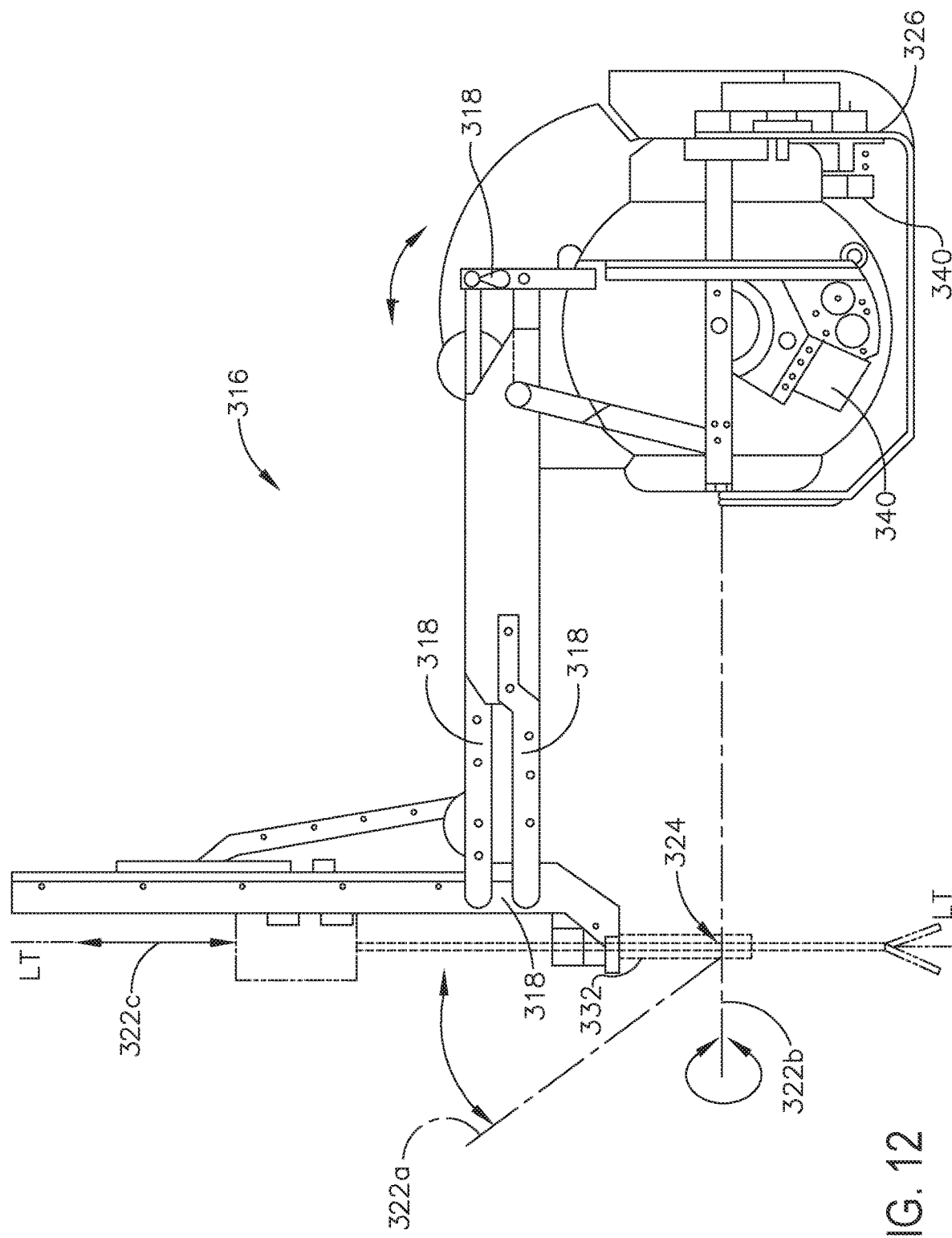
FIG. 12 is a side view of the robotic surgical arm cart/manipulator depicted in FIG. 11 according to one aspect of this disclosure.

Various embodiments disclosed herein may be employed in connection with a robotic system 300 of the type depicted in FIGS. 10-12, for example. FIG. 10 depicts one version of a master controller 301 that may be used in connection with a robotic arm slave cart 310 of the type depicted in FIG. 11. Master controller 301 and robotic arm slave cart 310, as well as their respective components and control systems are collectively referred to herein as a robotic system 300. Examples of such systems and devices are disclosed in U.S. Pat. No. 7,524,320, entitled MECHANICAL ACTUATOR INTERFACE SYSTEM FOR ROBOTIC SURGICAL TOOLS, as well as U.S. Pat. No. 9,072,535, entitled SURGICAL STAPLING INSTRUMENTS WITH ROTATABLE STAPLE DEPLOYMENT ARRANGEMENTS, which are each hereby incorporated by reference herein in their respective entireties. Thus, various details of such devices will not be described in detail herein beyond that which may be necessary to understand various embodiments and forms of the present disclosure. As is known, the master controller 301 generally includes master controllers (generally represented as 303 in FIG. 10) which are grasped by the surgeon and manipulated in space while the surgeon views the procedure via a stereo display 302. The master controllers 301 generally comprise manual input devices which preferably move with multiple degrees of freedom, and which often further have an actuatable handle for actuating tools (for example, for closing grasping jaws, applying an electrical potential to an electrode, or the like).

As can be seen in FIG. 11, in one form, the robotic arm cart 310 may be configured to actuate one or more surgical tools, generally designated as 330. Various robotic surgery systems and methods employing master controller and robotic arm cart arrangements are disclosed in U.S. Pat. No. 6,132,368, entitled MULTI-COMPONENT TELEPRESENCE SYSTEM AND METHOD the entire disclosure of which is hereby incorporated by reference herein. In various forms, the robotic arm cart 310 includes a base 312 from which, in the illustrated embodiment, surgical tools may be supported. In various forms, the surgical tool(s) may be supported by a series of manually articulatable linkages, generally referred to as set-up joints 314, and a robotic manipulator 316. In various embodiments, the linkage and joint arrangement may facilitate rotation of a surgical tool around a point in space, as more fully described in issued U.S. Pat. No. 5,817,084, entitled REMOTE CENTER POSITIONING DEVICE WITH FLEXIBLE DRIVE, the entire disclosure of which is hereby incorporated by reference herein. The parallelogram arrangement constrains rotation to pivoting about an axis 322*a*, sometimes called the pitch axis. The links supporting the parallelogram linkage are pivotally mounted to set-up joints 314 (FIG. 11) so that the surgical tool further rotates about an axis 322*b*, sometimes called the yaw axis. The pitch and yaw axes 322*a*, 322*b* intersect at the remote center 324, which is aligned along an elongate shaft of a surgical tool. The surgical tool may have further degrees of driven freedom as supported by manipulator 316, including sliding motion of the surgical tool along the longitudinal axis "LT-LT". As the surgical tool slides along the tool axis LT-LT relative to manipulator 316 (arrow 322*c*), remote center 324 remains fixed relative to base 326 of manipulator 316. Hence, the entire manipulator is generally moved to re-position remote center 324. Linkage 318 of manipulator 316 may be driven by a series of motors 340. These motors actively move linkage 318 in response to commands from a processor of a control system. The motors 340 may also be employed to manipulate the surgical tool. Alternative joint structures and set up arrangements are also contemplated. Examples of other joint and set up arrangements, for example, are disclosed in U.S. Pat. No. 5,878,193, entitled AUTOMATED ENDOSCOPE SYSTEM FOR OPTIMAL POSITIONING, the entire disclosure of which is hereby incorporated by reference herein. Additionally, while the data communication between a robotic component and the processor of the robotic surgical system is primarily described herein with reference to communication between the surgical tool and the master controller 301, it should be understood that similar communication may take place between circuitry of a manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like. In accordance with at least one aspect, various surgical instruments disclosed herein may be used in connection with other robotically-controlled or automated surgical systems and are not necessarily limited to use with the specific robotic system components shown in FIGS. 10-12 and described in the aforementioned references.

Figure 13:
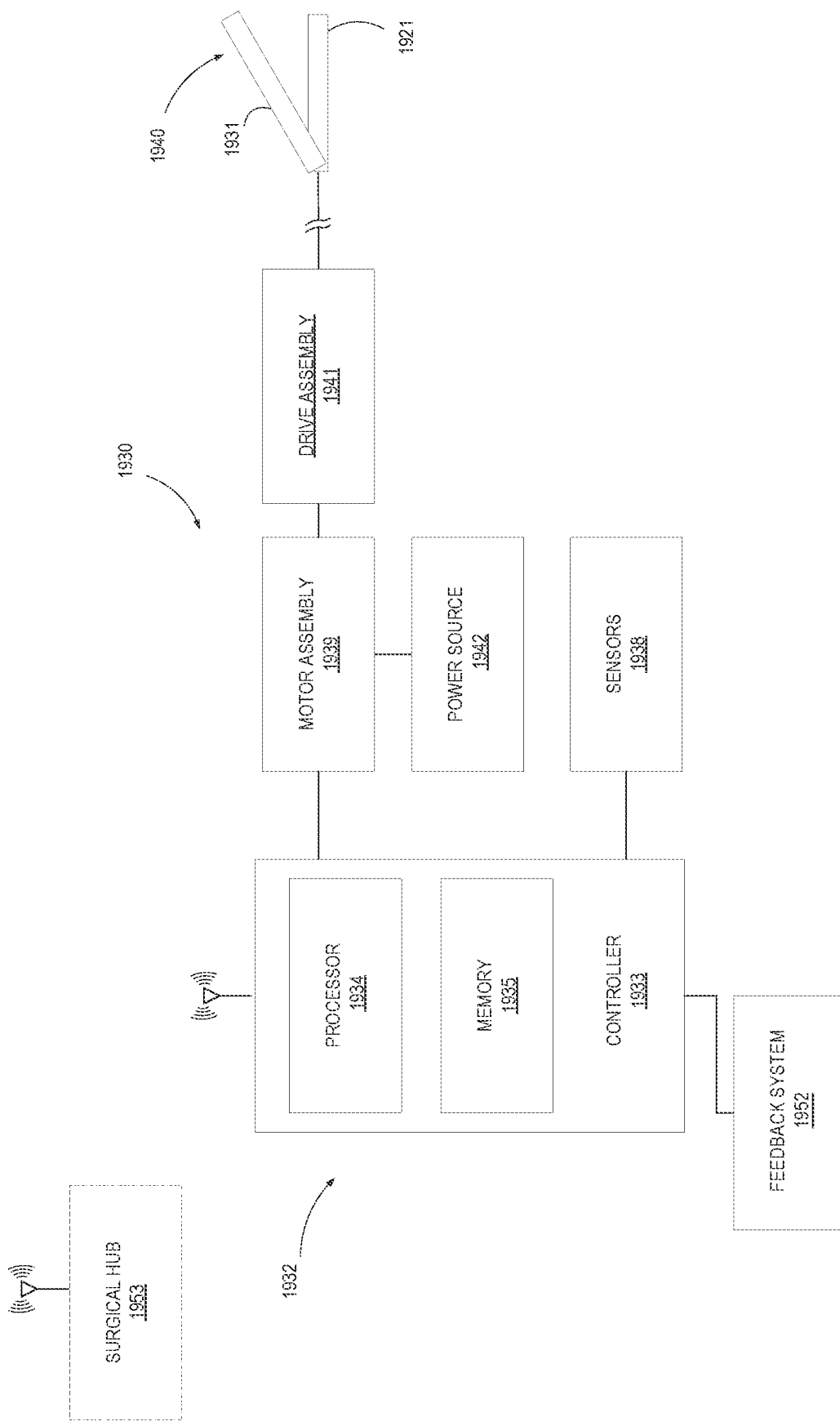
FIG. 13 illustrates a block diagram of a surgical system for use with one or more surgical instruments, tools, and/or robotic systems in accordance with one or more aspects of the present disclosure.

FIG. 13 illustrates a block diagram of a surgical system 1930 for use with one or more surgical instruments, tools, and/or robotic systems in accordance with one or more aspects of the present disclosure. The system 1930 includes a control circuit 1932. The control circuit 1932 includes a microcontroller 1933 comprising a processor 1934 and a storage medium such as, for example, a memory 1935.

A motor assembly 1939 includes one or more motors, driven by motor drivers. The motor assembly 1939 operably couples to a drive assembly 1941 to drive, or effect, one or more motions at an end effector 1940. The drive assembly 1941 may include any number of components suitable for transmitting motion to the end effector 1940 such as, for example, one or more linkages, bars, tubes, and/or cables, for example.

One or more of sensors 1938, for example, provide real-time feedback to the processor 1934 about one or more operational parameters monitored during a surgical procedure being performed by the surgical system 1930. The operational parameters can be associated with a user performing the surgical procedure, a tissue being treated, and/or one or more components of the surgical system 1930, for example. The sensor 1938 may comprise any suitable sensor, such as, for example, a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor.

Further to the above, in various arrangements, the sensors 1938 may comprise any suitable sensor for detecting one or more conditions at the end effector 1940 including, without limitation, a tissue thickness sensor such as a Hall Effect Sensor or a reed switch sensor, an optical sensor, a magneto-inductive sensor, a force sensor, a pressure sensor, a piezo-resistive film sensor, an ultrasonic sensor, an eddy current sensor, an accelerometer, a pulse oximetry sensor, a temperature sensor, a sensor configured to detect an electrical characteristic of a tissue path (such as capacitance or resistance), or any combination thereof. As another example, and without limitation, the sensors 1938 may include one or more sensors located at, or about, an articulation joint extending proximally from the end effector 1940. Such sensors may include, for example, a potentiometer, a capacitive sensor (slide potentiometer), piezo-resistive film sensor, a pressure sensor, a pressure sensor, or any other suitable sensor type. In some arrangements, the sensor 1938 may comprise a plurality of sensors located in multiple locations in the end effector 1940.

In certain aspects, the system 1930 includes a feedback system 1952 which includes one or more devices for providing a sensory feedback to a user. Such devices may comprise, for example, visual feedback devices (e.g., an LCD display screen, a touch screen, LED indicators), audio feedback devices (e.g., a speaker, a buzzer) or tactile feedback devices (e.g., haptic actuators).

The microcontroller 1933 may be programmed to perform various functions such as precise control over the speed and position of the drive assembly 1941. In one aspect, the microcontroller 1933 may be any single-core or multicore processor such as those known under the trade name ARM Cortex by Texas Instruments. In one aspect, the main microcontroller 1933 may be an LM4F230H5QR ARM Cortex-M4F Processor Core, available from Texas Instruments, for example, comprising an on-chip memory of 256

KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

The microcontroller 1933 may be configured to compute a response in the software of the microcontroller 1933. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

The motor assembly 1939 includes one or more electric motors and one or more motor drivers. The electric motors can be in the form of a brushed direct current (DC) motor with a gearbox and mechanical links to the drive assembly 1941. In one aspect, a motor driver may be an A3941 available from Allegro Microsystems, Inc.

In various forms, the motor assembly 1939 includes a brushed DC driving motor having a maximum rotational speed of approximately 25,000 RPM. In other arrangements, the motor assembly 1939 may include a brushless motor, a cordless motor, a synchronous motor, a stepper motor, or any other suitable electric motor. The motor driver may comprise an H-bridge driver comprising field-effect transistors (FETs), for example.

The motor assembly 1939 can be powered by a power source 1942. In certain aspects, the power source 1942 includes one or more batteries which may include a number of battery cells connected in series that can be used as the power source to power the motor assembly 1939. In certain circumstances, the battery cells of the power assembly may be replaceable and/or rechargeable. In at least one example, the battery cells can be lithium-ion batteries which can be couplable to and separable from the power assembly.

Further to the above, the end effector 1940 includes a first jaw 1921 and a second jaw 1931. At least one of the first jaw 1921 and the second jaw 1931 is rotatable relative to the other during a closure motion that transitions the end effector 1940 from an open configuration toward a closed configuration. The closure motion may cause the jaws 1921, 1931 to grasp tissue therebetween. In certain arrangements, sensor s, such as, for example, a strain gauge or a micro-strain gauge, are configured to measure one or more parameters of the end effector 1940, such as, for example, the amplitude of the strain exerted on the one or both of the jaws 1921, 1931 during a closure motion, which can be indicative of the closure forces applied to the jaws 1921, 1931. The measured strain is converted to a digital signal and provided to the processor 1934, for example. Alternatively, additionally, sensors such as, for example, a load sensor, can measure a closure force and/or a firing force applied to the jaws 1921, 1931.

In various arrangements, a current sensor can be employed to measure the current drawn by a motor of the motor assembly 1939. The force required to advance the drive assembly 1941 can correspond to the current drawn by the motor, for example. The measured force is converted to a digital signal and provided to the processor 1934.

In one form, strain gauge sensors can be used to measure the force applied to the tissue by the end effector 1940, for example. A strain gauge can be coupled to the end effector 1940 to measure the force on the tissue being treated by the end effector 1940. In one aspect, the strain gauge sensors can measure the amplitude or magnitude of the strain exerted on a jaw of an end effector 1940 during a closure motion which can be indicative of the tissue compression. The measured strain is converted to a digital signal and provided to a processor 1934.

The measurements of the tissue compression, the tissue thickness, and/or the force required to close the end effector on the tissue, as respectively measured by the sensors 1938 can be used by the microcontroller 1933 to characterize the selected position of one or more components of the drive assembly 1941 and/or the corresponding value of the speed of one or more components of the drive assembly 1941. In one instance, a memory (e.g. memory 1935) may store a technique, an equation, and/or a lookup table which can be employed by the microcontroller 1933 in the assessment.

The system 1930 may comprise wired or wireless communication circuits to communicate with surgical hubs (e.g. surgical hub 1953), communication hubs, and/or robotic surgical hubs, for example. Additional details about suitable interactions between a system 1930 and the surgical hub 1953 are disclosed in are disclosed in U.S. patent application Ser. No. 16/209,423 entitled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Patent Application Publication No. 2019/0200981, the entire disclosure of which is incorporated by reference in its entirety herein.

In various aspects, the control circuit 1932 can be configured to implement various processes described herein. In certain aspects, the control circuit 1932 may comprise a microcontroller comprising one or more processors (e.g., microprocessor, microcontroller) coupled to at least one memory circuit. The memory circuit stores machine-executable instructions that, when executed by the processor, cause the processor to execute machine instructions to implement various processes described herein. The processor may be any one of a number of single-core or multicore processors known in the art. The memory circuit may comprise volatile and non-volatile storage media. The processor may include an instruction processing unit and an arithmetic unit. The instruction processing unit may be configured to receive instructions from the memory circuit of this disclosure.

Alternatively, in certain instances, the control circuit 1932 can be in the form of a combinational logic circuit configured to implement various processes described herein. The combinational logic circuit may comprise a finite state machine comprising a combinational logic configured to receive data, process the data by the combinational logic, and provide an output.

Alternatively, in certain instances, the control circuit 1932 can be in the form of a sequential logic circuit. The sequential logic circuit can be configured to implement various processes described herein. The sequential logic circuit may comprise a finite state machine. The sequential logic circuit may comprise a combinational logic, at least one memory circuit, and a clock, for example. The at least one memory circuit can store a current state of the finite state machine. In certain instances, the sequential logic circuit may be synchronous or asynchronous. In other instances, the control circuit 1932 may comprise a combination of a processor (e.g., processor 1934) and a finite state machine to implement various processes herein. In other aspects, the finite state machine may comprise a combination of a combinational logic circuit (and the sequential logic circuit, for example.

Figure 14:
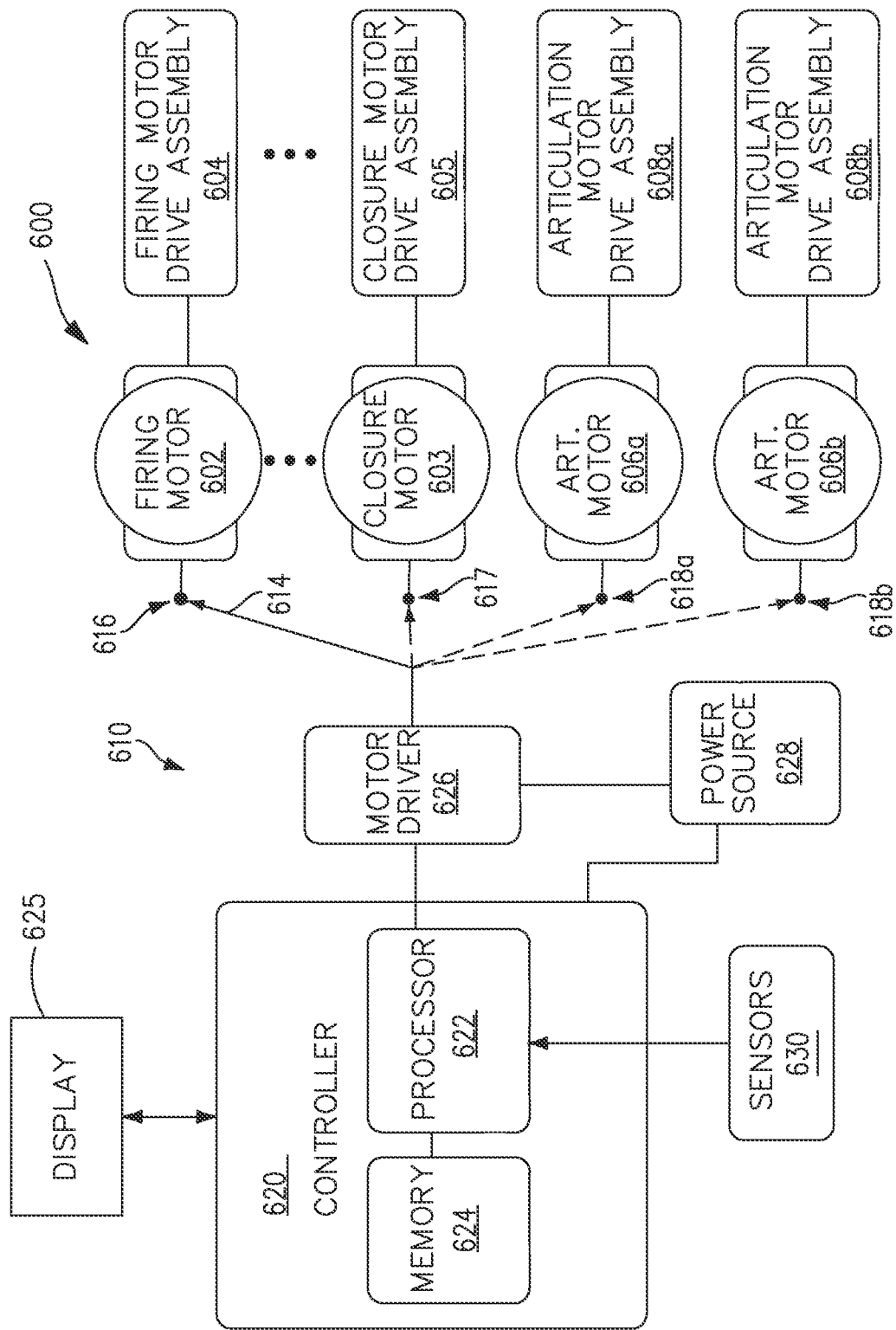
FIG. 14 illustrates a block diagram of a surgical system for use with one or more surgical instruments, tools, and/or robotic systems in accordance with one or more aspects of the present disclosure.

FIG. 14 illustrates a block diagram of a surgical system 600 for use with one or more surgical instruments, tools, and/or robotic systems in accordance with one or more aspects of the present disclosure. The surgical system 600 is similar in many respects to the surgical system 1930, which are not repeated herein at the same of detail for brevity. For example, like the surgical system 1930, the surgical system 600 includes a control circuit comprising a microcontroller 620 comprising a processor 622 and a memory 624, sensors 630, and a power source 628, which are similar, respectively, to the microcontroller 1933, the processor 1934, the memory 1935, and the power source 1942. Additionally, the surgical system 600 includes a plurality of motors and corresponding driving assemblies that can be activated to perform various functions.

In certain instances, a first motor can be activated to perform a first function, a second motor can be activated to perform a second function, a third motor can be activated to perform a third function, a fourth motor can be activated to perform a fourth function, and so on. In certain instances, the plurality of motors can be individually activated to cause firing, closure, and/or articulation motions in an end effector 1940, for example. The firing, closure, and/or articulation motions can be transmitted to the end effector 1940 through a shaft assembly, for example.

In certain instances, the system 600 may include a firing motor 602. The firing motor 602 may be operably coupled to a firing motor drive assembly 604 which can be configured to transmit firing motions, generated by the motor 602 to the end effector, in particular to displace the I-beam element. In certain instances, the firing motions generated by the motor 602 may cause the staples to be deployed from a staple cartridge into tissue captured by the end effector 1940 and/or the cutting edge of the I-beam element to be advanced to cut the captured tissue, for example. The I-beam element may be retracted by reversing the direction of the motor 602.

In certain instances, the system 600 may include a closure motor 603. The closure motor 603 may be operably coupled to a closure motor drive assembly 605 which can be configured to transmit closure motions, generated by the motor 603 to the end effector 1940, in particular to displace a closure tube to close an anvil and compress tissue between the anvil and the staple cartridge. The closure motions may cause the end effector 1940 to transition from an open configuration to an approximated configuration to grasp tissue, for example. The end effector 1940 may be transitioned to an open position by reversing the direction of the motor 603.

In certain instances, the system 600 may include one or more articulation motors 606a, 606b, for example. The motors 606a, 606b may be operably coupled to respective articulation motor drive assemblies 608a, 608b, which can be configured to transmit articulation motions generated by the motors 606a, 606b to the end effector. In certain instances, the articulation motions may cause the end effector to articulate relative to a shaft, for example.

As described above, the system 600 may include a plurality of motors which may be configured to perform various independent functions. In certain instances, the plurality of motors of the surgical instrument or tool can be individually or separately activated to perform one or more functions while the other motors remain inactive. For example, the articulation motors 606a, 606b can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore, the closure motor 603 may be activated simultaneously with the firing motor 602 to cause the closure tube and the I-beam element to advance distally as described in more detail hereinbelow.

In certain instances, the system 600 may include a common control module 610 which can be employed with a plurality of motors of the surgical instrument or tool. In certain instances, the common control module 610 may accommodate one of the plurality of motors at a time. For example, the common control module 610 can be couplable to and separable from the plurality of motors of the robotic surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606a, 606b and operable engagement with either the firing motor 602 or the closure motor 603. In at least one example, as illustrated in FIG. 14, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618a, the switch 614 may electrically couple the common control module 610 to the first articulation motor 606a; and in a fourth position 618b, the switch 614 may electrically couple the common control module 610 to the second articulation motor 606b, for example. In certain instances, separate common control modules 610 can be electrically coupled to the firing motor 602, the closure motor 603, and the articulations motor 606a, 606b at the same time. In certain instances, the switch 614 may be a mechanical switch, an electromechanical switch, a solid-state switch, or any suitable switching mechanism.

Each of the motors 602, 603, 606a, 606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 14, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described above.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610.

In certain instances, the memory 624 may include program instructions for controlling each of the motors of the surgical instrument 600 that are couplable to the common control module 610. For example, the memory 624 may include program instructions for controlling the firing motor 602, the closure motor 603, and the articulation motors 606*a*, 606*b*. Such program instructions may cause the processor 622 to control the firing, closure, and articulation functions in accordance with inputs from algorithms or control programs of the surgical instrument or tool.

In certain instances, one or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the I-beam of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618*a*, 618*b*.

In various instances, as illustrated in FIG. 14, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described above.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610.

In certain instances, the memory 624 may include program instructions for controlling each of the motors of the surgical instrument that are couplable to the common control module 610. For example, the memory 624 may include program instructions for controlling the firing motor 602, the closure motor 603, and the articulation motors 606*a*, 606*b*. Such program instructions may cause the processor 622 to control the firing, closure, and articulation functions in accordance with inputs from algorithms or control programs of the surgical instrument or tool.

Figure 15:
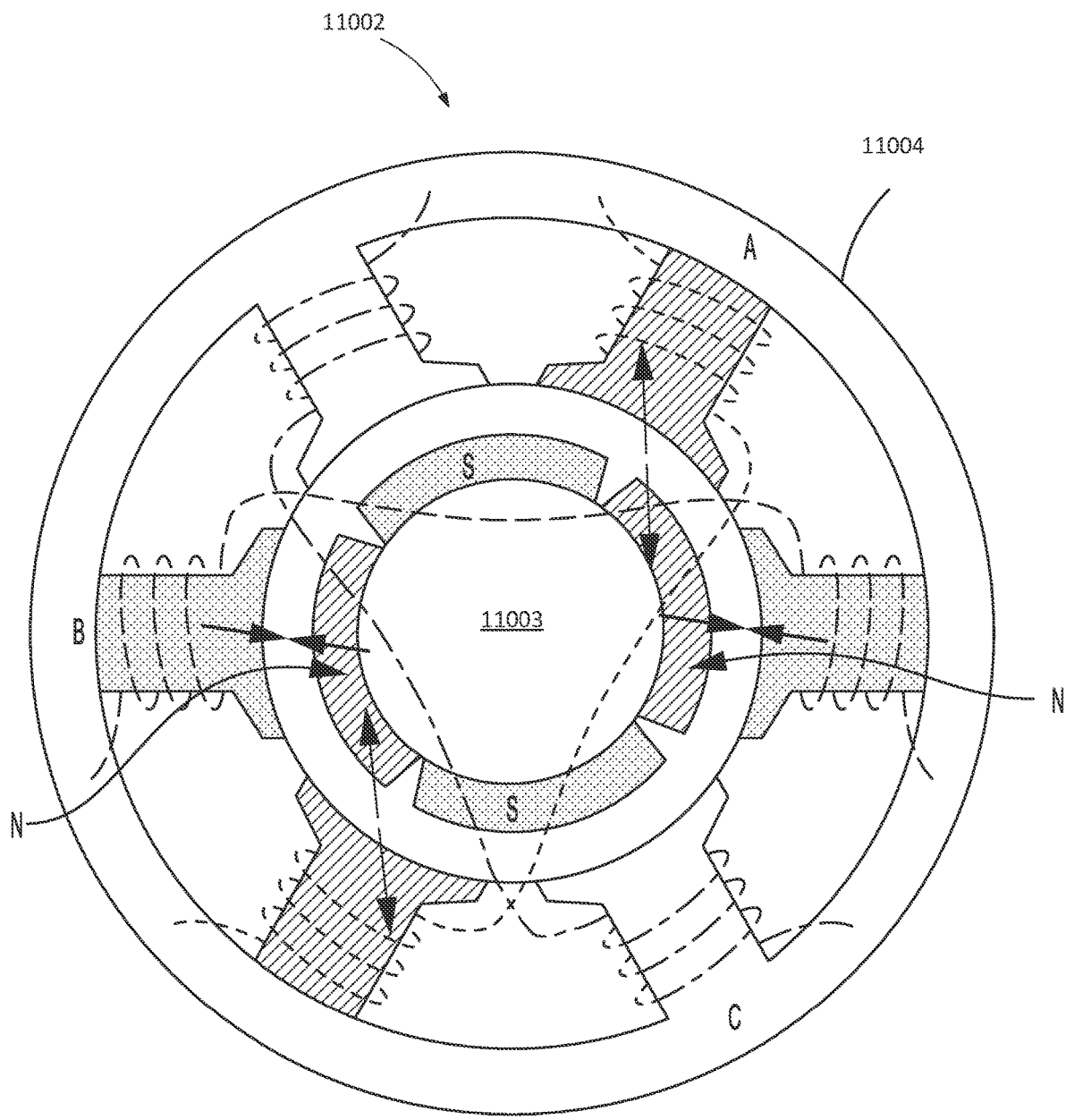
FIG. 15 illustrates a motor, in accordance with at least one aspect of the present disclosure.

In various instances, referring primarily to FIG. 13 and FIG. 15, a surgical system 1930 adaptively controls a motor 11002, for example, independent of, or in absence of, a motor drive signal that motivates the motor 11002 to effect a tissue treatment motion of the end effector 1940, for example. As described in greater detail elsewhere herein, a control circuit (e.g. microcontroller 1933, 620) may cause a motor drive signal to be transmitted from a power source (e.g. 1942, 628) to the motor 11002, or any suitable motor of the motor assembly 1939, for example, to effect the tissue treatment motion. In one aspect, the motor can be a firing motor that motivates a firing drive assembly to deploy staples from the end effector 1940 into tissue grasped by the end effector 1940, and optionally cut the tissue. In one aspect, the motor can be a closure motor that motivates one or more jaws of the end effector 1940 to transition toward a closed configuration to grasp tissue. In one aspect, the motor can be an articulation motion that motivates an articulation of the end effector about an articulation joint, for example. In one aspect, the motor can be a rotation motor that motivates a rotation of the end effector 1940 about a longitudinal axis.

Further to the above, the adaptive control of the motor 11002, for example, independent of, or in absence of, the motor drive signal facilitates an additional layer of motor control beyond, or in addition to, the control afforded by the motor drive signal. In various instances, the adaptive control of the motor 11002 is achieved by an adaptation, or adjustment, of elements of a motor drive circuit of the motor assembly 1939, or motor driver 626, for example, by a control circuit (e.g. microcontroller 1933, 620), for example, to control motor performance in absence of the motor drive signal.

In one aspect, the motor drive circuit is adjusted by the control circuit, in the absence of the motor drive signal, while the motor is in a dynamic state, to control deceleration of the motor, for example. In one aspect, the control circuit adaptively effects modifications to parameters of the motor drive signal, and adjustments to electronics of the motor drive circuit in the absence of the motor drive signal, to control performance of the motor during a tissue treatment motion, for example. In certain instances, the adaptive adjustment, or control, of the motor drive circuit by the control circuit yields a dynamic braking mode, an active braking mode, a coasting mode, or a combination thereof, as described in greater detail below. In certain instances, the control circuit achieves a desired deceleration, in absence of the motor drive signal, by adjusting the electronics of the motor drive circuit to generate a resistance to the dynamic inertia of the motor, by activating, for example, the dynamic braking mode, the active braking mode, the coasting braking mode, or a combination thereof, of the electronics of the motor drive circuit.

Figure 16:
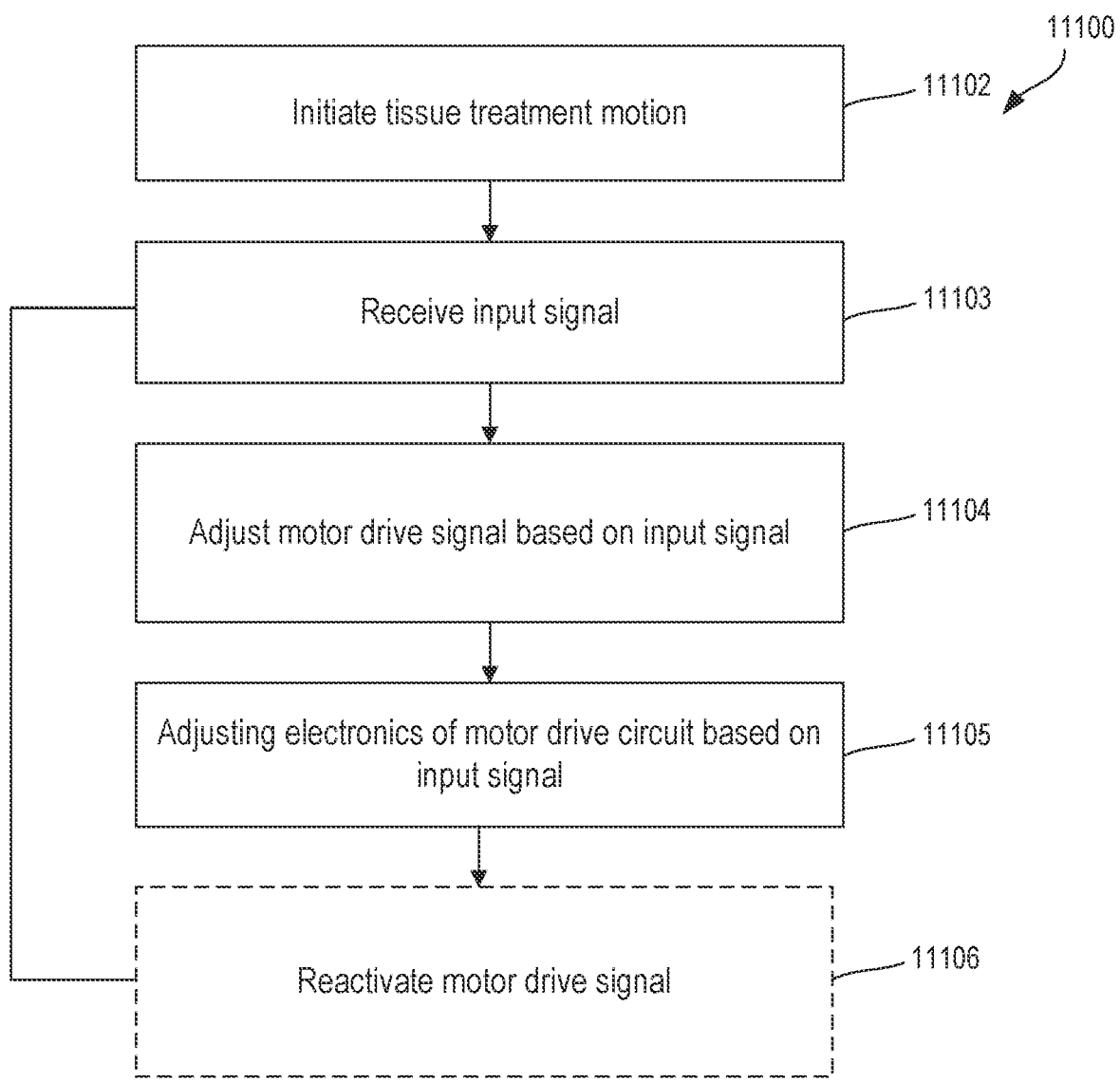
FIG. 16 is a flow diagram illustrating a method for controlling electronics of a motor drive circuit of a motor in absence of the motor drive signal, in accordance with at least one aspect of the present disclosure.

In one aspect, the control circuit adaptively effects modifications to parameters of the motor drive signal, and adjustments to electronics of the motor drive circuit in absence of the motor drive signal, the modifications and/or adjustments based on one or parameters known, measured, and/or monitored by the sensors 1938, for example. FIG. 16 is a flow diagram illustrating a method 11100 for controlling electronics of motor drive circuit of a motor (e.g. motor 11002) of the motor assembly 1939, in absence of the motor drive signal. The method 11100 can be implemented by any suitable control circuit (e.g. microcontroller 1933, 620). In the illustrated example, the method 11100 includes initiating 11102, for example by the control circuit, a tissue-treatment motion of a surgical system 1930, for example. In one exemplification, the control circuit causes the power source 1942 to transmit a motor drive signal to the motor by way of the motor drive circuit to cause the motor to advance the drive assembly 1941 to effect the tissue treatment motion (e.g. closure, firing, rotation, articulation) at the end effector 1940, for example.

The method 11100 further includes receiving 11103 an input signal from one or more of the sensors 1938 and/or the surgical hub 1953 indicative of one or more parameters of the tissue, the motor assembly 1939, drive assembly 1941, and/or the end effector 1940. In certain aspects, the input signal is indicative of a tissue property such as, for example, tissue thickness, tissue type, and/or tissue impedance. In certain aspects, the input signal is indicative of a parameter of an inertia, a frictional loss, a tolerance stack, a tissue creep, for example.

The method further includes adjusting 11104 the motor drive signal based on the input signal. In one exemplification, the control circuit deactivates, or cuts off, the motor drive signal based on the input signal, which can be a temporary deactivation. In another exemplification, the control circuit increases a parameter of the motor drive signal, then decreases the same parameter, or another parameter, of the motor drive signal. In another exemplification, the control circuit maintains the motor drive signal at a current level, for example by interrupting an increase in the motor drive signal set by a default control program, and then executes a following decrease in the motor drive signal. Other suitable adjustments 11104 in response to the input signal are contemplated by the present disclosure.

The method 11100 further includes adjusting 11105, modifying, or adapting electronics of the motor drive circuit, in absence of the motor drive signal, to adjust motor performance based on the input signal. In certain instances, adjusting the electronics of the motor drive circuit comprises generating a resistance to the dynamic inertia of the motor, by activating, for example, the dynamic braking mode, the active braking mode, the coasting braking mode, or a combination thereof, of the electronics of the motor drive circuit.

Further to the above, in certain instances, the method 11100 may further include reactivating 11106, for example by the control circuit, the motor drive signal based on the input signal. The process 11100 is repeated with receipt of an input signal indicative of a change in the monitored parameter or a different parameter. In one exemplification, the input signal indicates a change in the monitored parameter that gave rise to the adjustments, which causes the control circuit to reactivate the motor drive signal in accordance with the default control program of the tissue treatment motion.

In certain instances, the adaptive control is based on a tissue property such as, for example, tissue thickness, tissue type, and/or tissue impedance. In such instances, the control circuit initiates a firing stroke to seal, by staples or energy application, and cut tissue grasped by the end effector 1940. During the firing stroke the control circuit receives input from the sensors 1938 indicative of a tissue thickness, and determines that the received tissue thickness is of a magnitude beyond an acceptable threshold associated with the current speed of the motor. Such determination can be achieved by way of a predetermined threshold, an equation, and/or a look-table, for example, stored in a memory communicably coupled with the control circuit. Based on the determination, the control circuit temporarily cuts off the motor drive signal, and adjusts the electronics of the motor drive circuit to execute the dynamic braking mode, the active braking mode, the coasting braking mode, or a combination thereof, to reduce the speed of the motor to an acceptable speed based on the detected tissue thickness. In certain instances, the control circuit adjusts the electronics of the motor drive signal to generate sufficient resistance to the dynamic inertia of the motor to ensure reaching the acceptable speed before the firing stroke reaches the tissue portion possessing the detected tissue thickness.

In certain instances, the control circuit incrementally, and slightly, increases the speed of the motor to test whether the capacity of the motor is capable of accommodating a speed adjustment. In such instances, the control circuit incrementally modifies the motor drive signal, while receiving sensor input regarding the resulting speed of the motor. If the control circuit determines that an incremental increase is beyond the capacity of the motor, the control circuit may respond by temporarily cutting off the motor drive signal. In such instances, the control circuit may switch to performing adjustments of the electronics of the motor drive circuit to implement further manipulations of the motor speed, in the absence of the motor drive signal, to yield a deceleration, for example, to a speed within the capacity of the motor. At such point, the motor drive signal can be reactivated, and the adjustments to the electronics of the motor drive circuit stopped.

Figure 17:
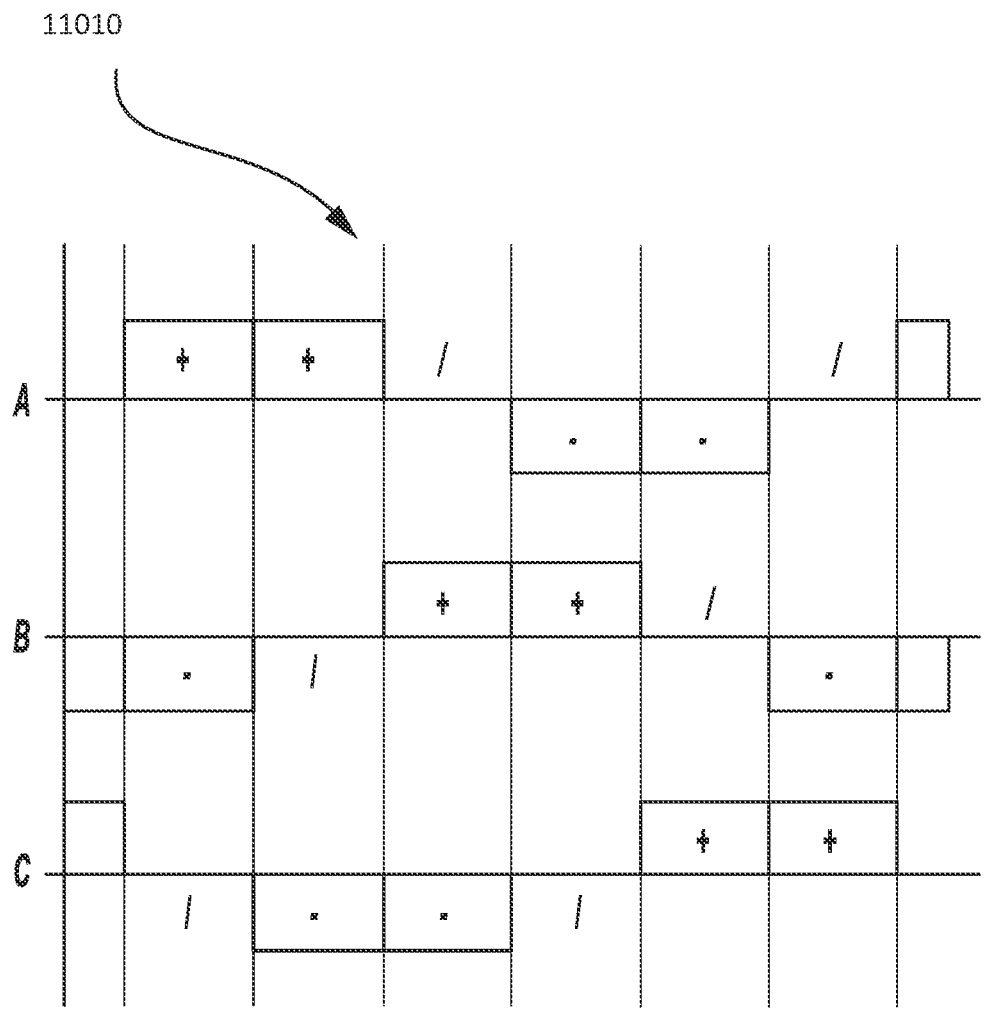
FIG. 17 illustrates a motor drive signal, in accordance with at least one aspect of the present disclosure.

Referring to FIG. 15 and FIG. 17, one or more of the methods described herein can be implemented to control performance of a brushless motor such as, for example, the motor 11002 to effect a tissue treatment motion. As previously discussed, the performance of the motor 11002 can be controlled by adjusting the motor drive signal, and in the absence of the motor drive signal, by adjusting electronics of the motor drive circuit. FIG. 17 illustrates an exemplification of a motor drive signal for the motor 11002. In the illustrated example, the motor drive signal is defined by a motor current waveform 11010 configured to generate a rotational drive motion of the motor 11002.

In the illustrated example, the motor 11002 is a brushless DC (BLDC) motor that includes a rotor 11003 and a stator 11004. The stator 11004 includes three electromagnet pairs A, B, C disposed around the rotor 11003 which includes permanent magnets disposed around a rotatable shaft. While an inrunner motor is depicted, it is understood that the BLDC motor 11002 can be an outrunner motor, for example. Moreover, other types of suitable motors are contemplated by the present disclosure. In order to increase the efficiency of the motor 11002, two opposite coils are wound as a single coil that generates each of the electromagnet pairs A, B, C.

As shown in FIG. 15, the rotor 11003 includes a plurality of poles alternating between North and South. In operation, the electromagnet pairs A, B, C around the rotor 11003 are alternated between high, low, and inactive in a sequenced manner, as illustrated in FIG. 17, for example, which causes the rotor 11003 to move from one position to the next in a rotational drive motion due to sequenced attraction and repulsion forces. The current flowing through the electromagnet pairs A, B, C dictates the polarity of the electromagnet pairs A, B, C, thereby generating an alternating attraction and repulsion forces that cooperatively yield the rotational drive motion of the rotor 11003, and producing a controlled torque and discrete stopping and/or holding positions.

While the motor 11002 is illustrated with three electromagnet pairs A, B, C, this is not limiting. Other embodiment of the present disclosure can include motors with more or less electromagnet pairs and more or less permanent magnets in any arrangement suitable for balancing attraction and repulsion over small increments of the rotor motion.

Figure 18:
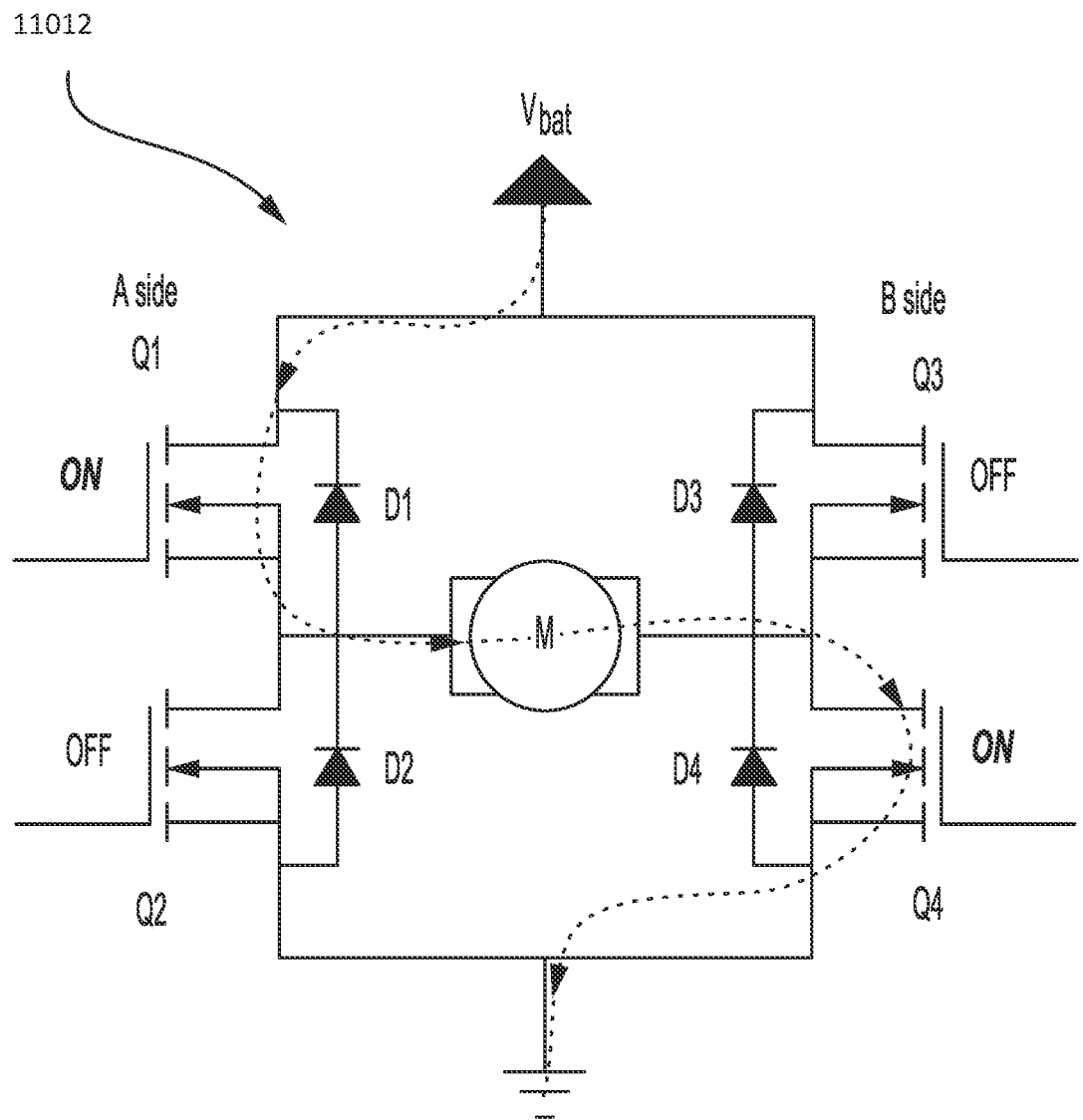
FIG. 18 is an H-Bridge FETs circuit in a drive mode, in accordance with at least one aspect of the present disclosure.
Figure 19:
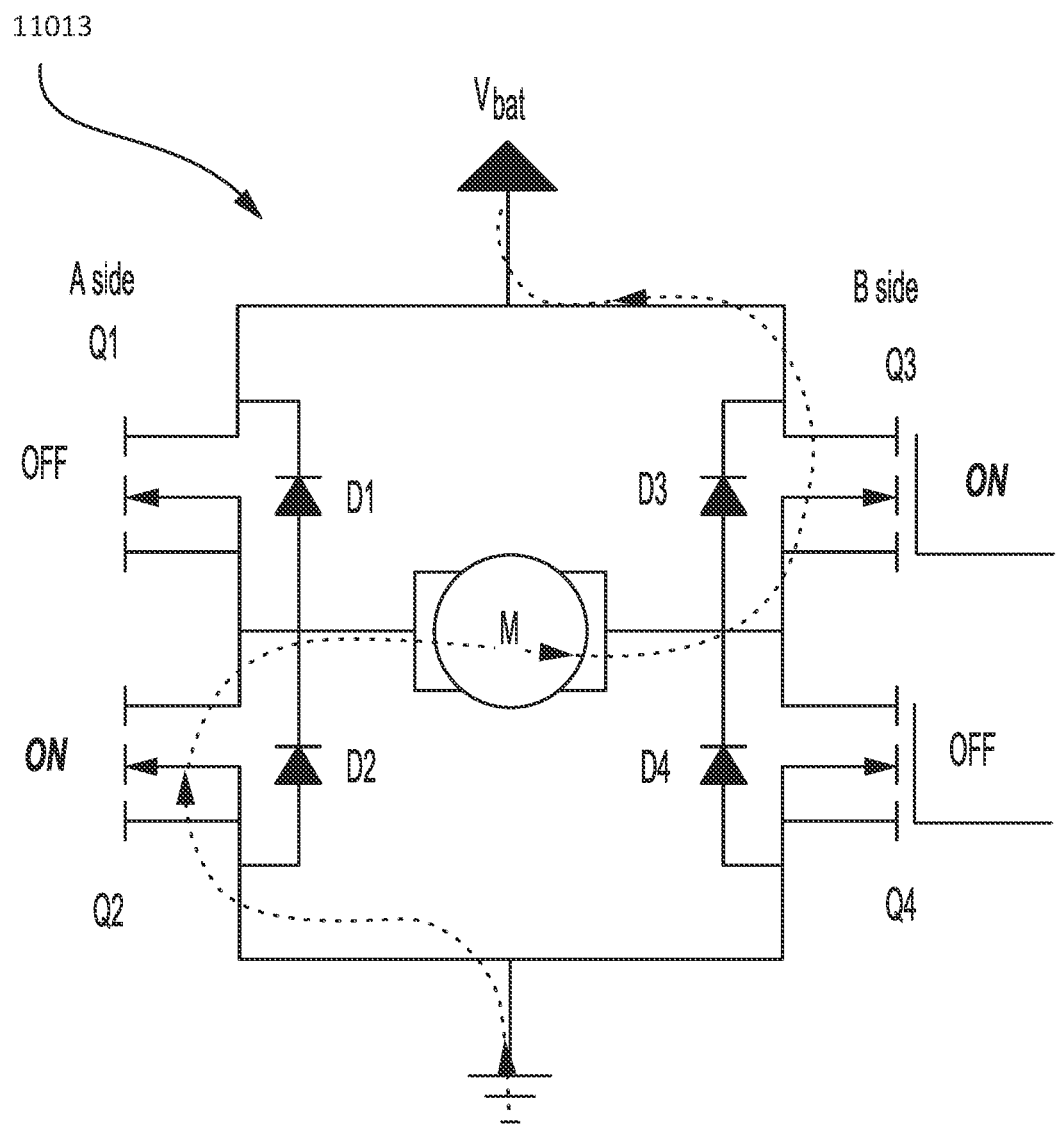
FIG. 19 is an H-Bridge FETs circuit in a reverse mode, in accordance with at least one aspect of the present disclosure.
Figure 20:
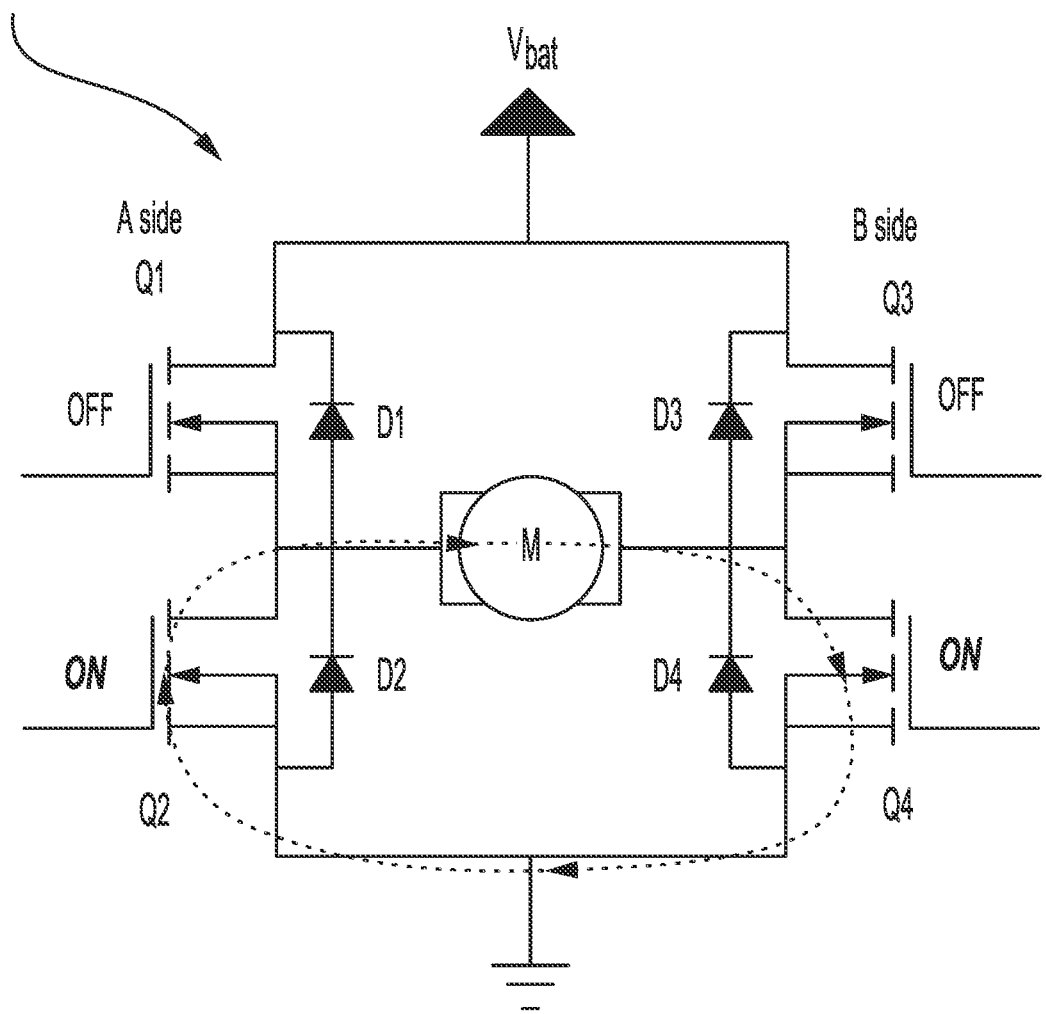
FIG. 20 is an H-Bridge FETs circuit in a dynamic braking mode, in accordance with at least one aspect of the present disclosure.

In various instances, the motor assembly 1939 includes one or more H-Bridge FETs that are controlled by the control circuit to implement a motor drive sequence, in accordance with FIG. 17, for example. FIGS. 18-20 illustrate an example H-Bridge FETs in three phases: a positive phase, a negative phase, and an inactive phase. The control circuit selects the H-Bridge FETs phases per a predetermined sequence that yields the rotational drive motion of the rotor 11003. The power supply to the motor 11002 can continually increase the inertia of the drive assembly 1941. In certain instances, the inertia can be increased by one of the upper H-bridge FETs being open and one of the lower H-bridge FETs being open. The open FETs will correspond to the direction of the motion of the motor, as illustrated in FIGS. 18, 19, which yields a drive mode 11012 and an active reverse mode 11013, respectively.

As previously described, electronics of the motor drive circuit such as, for example, one or more of the H-Bridge FETs are adjusted by the control circuit independent, or in absence, of the motor drive signal, to adjust performance of the motor while in a dynamic state, for example. FIG. 20 presents an H-bridge FETs configuration implemented by the control circuit in the absence of the motor drive signal to yield an active or dynamic braking mode 11014. In the illustrated example, the upper H-bridge FETs are both open and the lower H-bridge FETs are both closed. In an alternative embodiment, an active or dynamic braking mode can also be achieved by the control circuit, in absence of the motor drive signal, by causing the upper H-bridge FETs to be open and the lower H-bridge FETs to be closed, for example.

The H-bridge FETs configuration illustrated in FIG. 20 yields the active or dynamic braking mode 11014, in the absence of the motor drive signal, which resists the inertia of the motor resulting in a discrete, quick, cessation of the rotational motion of the motor 11002. In the illustrated example, no applied voltage is present to force a rapid discharge of the current in the system. Accordingly, current dissipates slowly as heat, for example, as the current flows through the resistance of the inductor and the on-state resistance of the lower H-Bridge FETs. Despite the slower current decay, active braking mode provides a faster reduction in motor speed, due to the EMF generated by the decaying current.

Figure 21:
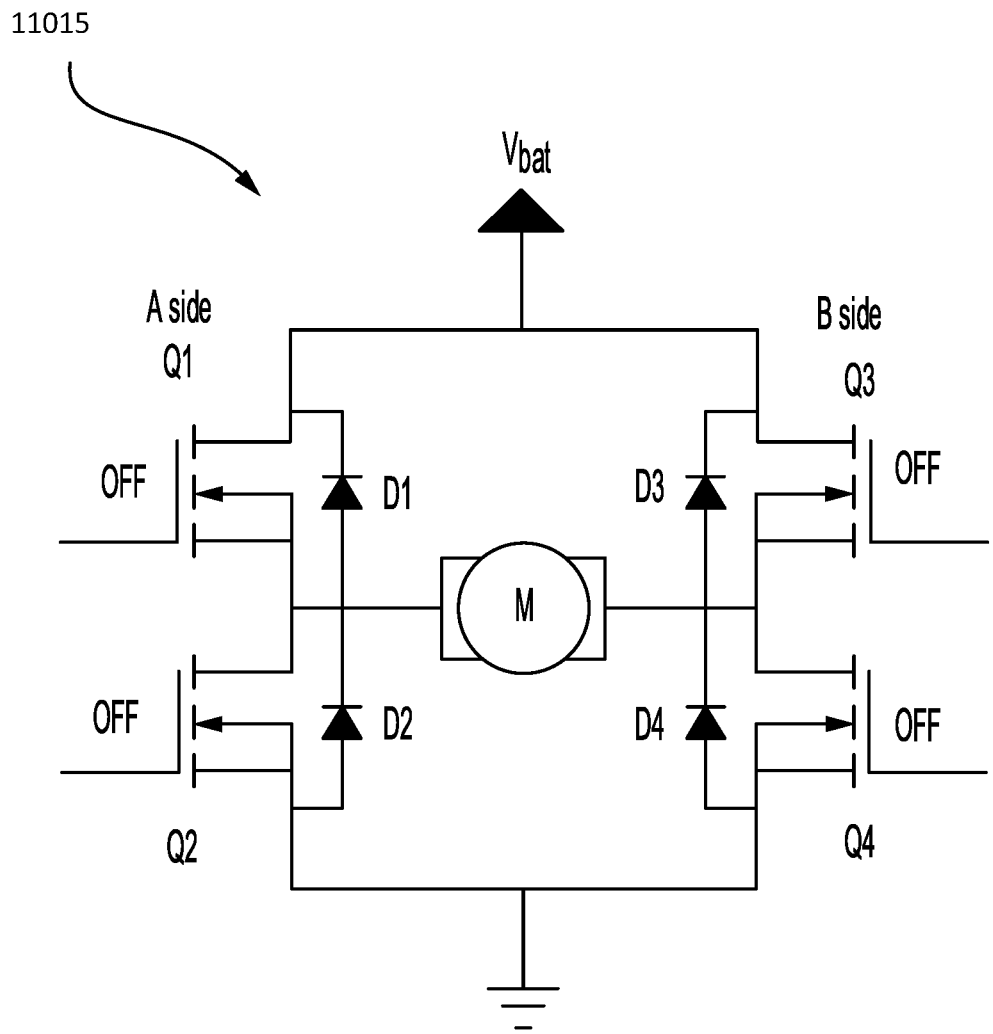
FIG. 21 is an H-Bridge FETs circuit in a coasting mode, in accordance with at least one aspect of the present disclosure.

FIG. 21 presents an H-bridge FETs configuration implemented by the control circuit in the absence of the motor drive signal to yield a passive braking, or coasting, mode 11015. In the illustrated example, the upper and lower H-bridge FETs are open in the passive braking, or coasting, mode, preventing current from the power source or any interactive motor current creation and braking. The system still brakes but based on the friction losses and inertia of the system. The removal of the motor drive signal, and the application of the passive braking, or coasting, mode can be beneficial in a closure tissue-treatment motion, for example.

The control circuit can initiate a closure tissue-treatment motion by causing a motor drive signal to be transmitted to a motor (e.g. motor 11002), in a drive mode 11012, to generate a rotational drive motion. A drive assembly (e.g. drive assembly 1941) causes at least one of the jaws of the end effector 1940 to move relative to the other jaw to grasp tissue. As the end effector 1940 transitions from an open configuration, see FIG. 13, toward a closed configuration, tissue between the jaws of the end effector 1940 is compressed. In certain instances, the control circuit deactivates, or cuts off, the motor drive signal, and then activates the passive braking, or coasting, mode 11015 to allow the compressed tissue to relax and/or push back against the drive assembly 1941.

In certain instances, the motor drive signal is based on a default control program. The default control program can be saved in a memory 1935, for example, and can be accessed by the control circuit for execution. The electronics of the motor drive circuit can be separately controlled by an adaptive motor control program. The adaptive motor control program can be adjusted based on measured parameters, such as data gathered by sensors 1938, for example. As previously described in greater detail, the adaptive motor control program may include one or more modes. The modes can be a driving mode 11012, a dynamic braking mode 11014, an active reverse mode 11013, a coasting braking mode 11015, or a combination thereof.

Various aspects of the subject matter described herein are set out in the following examples.

Example 1—A surgical system, comprising an end effector configurable between an open state and a clamped state. The end effector comprises a first jaw and a second jaw moveable relative to the first jaw. The surgical system further comprises a drive system, comprising a motor and a drive assembly movable by the motor to effect a tissue-treatment motion at the end effector. The surgical system further comprises a motor control system comprising motor control electronics. The motor control system is configured to transmit a motor drive signal that causes the motor to move the drive assembly to effect the tissue-treatment motion at the end effector and control the motor control electronics to modify the tissue-treatment motion independent of the motor drive signal.

Example 2—The surgical system of Example 1, wherein the motor drive signal is based on a default control program.

Example 3—The surgical system of Examples 1 or 2, wherein the motor control electronics are controlled by an adaptive motor control program.

Example 4—The surgical system of Example 3, wherein the adaptive motor control program comprises at least one of a dynamic braking mode, an active braking mode, or a coasting braking mode.

Example 5—The surgical system of any one of Examples 1-4, wherein the motor control system comprises at least one sensor configured to measure at least one parameter of the drive system.

Example 6—The surgical system of Example 5, wherein the motor control system controls the motor control electronics based on at least one reading of the at least one sensor.

Example 7—The surgical system of Examples 5 or 6, wherein the at least one parameter comprises a tissue creep parameter of the drive system, an inertia parameter of the drive system, or a friction loss parameter of the drive system.

Example 8—A surgical system, comprising an end effector configurable between an open state and a clamped state. The end effector comprises a first jaw, and a second jaw moveable relative to the first jaw. The surgical system further comprises a drive system, comprising a motor and a drive assembly movable by the motor to effect a tissue-treatment motion at the end effector. The surgical system further comprises a motor control system, comprising a motor drive circuit and a motor control circuit. The motor control circuit configured to cause a transmission of a motor drive signal through the motor driver circuit that causes the motor to move the drive assembly to effect the tissue-treatment motion at the end effector. The motor control circuit further configured to adaptively control elements of the motor drive circuit to control a deceleration of the motor in an absence of the motor drive signal.

Example 9—The surgical system of Example 8, wherein the motor drive signal is based on a default control program.

Example 10—The surgical system of Examples 8 or 9, wherein the elements of the motor drive circuit are controlled by an adaptive motor control program.

Example 11—The surgical system of Example 10, wherein the adaptive motor control program comprises at least one of a dynamic braking mode, an active braking mode, or a coasting braking mode.

Example 12—The surgical system of any one of Example 8-11, wherein the motor control system comprises at least one sensor configured to measure at least one parameter of the drive system.

Example 13—The surgical system of Example 12, wherein the motor control system controls the motor control electronics based on at least one reading of the at least one sensor.

Example 14—The surgical system of Examples 12 or 13, wherein the at least one parameter comprises a tissue creep parameter of the drive system, an inertia parameter of the drive system, or a friction loss parameter of the drive system.

Example 15—A surgical system, comprising an end effector configurable between an open state and a clamped state. The end effector comprises a first jaw and a second jaw moveable relative to the first jaw. The surgical system further comprises a drive system, comprising a motor and a drive assembly movable by the motor to effect a tissue-treatment motion at the end effector. The surgical system further comprises a sensor and a motor control system. The motor control system comprises a motor drive circuit and a control circuit. The control circuit configured to cause a transmission of a motor drive signal through the motor driver circuit that causes the motor to move the drive assembly to effect the tissue-treatment motion at the end effector, receive an input signal from the sensor, adjust the motor drive signal based on the input signal, and adaptively adjust elements of the motor drive circuit in an absence of the motor drive signal based on the input signal.

Example 16—The surgical system of Example 15, wherein adjusting the drive signal based on the input signal comprises deactivating the drive signal.

Example 17—The surgical system of Example 16, wherein the control circuit is further configured to reactivate the drive signal.

Example 18—The surgical system of any one of Example 15-17, wherein the motor drive signal is based on a default control program.

Example 19—The surgical system of any one of Examples 15-18, wherein the elements of the motor drive circuit are controlled by an adaptive motor control program.

Example 20—The surgical system of Example 19, wherein the adaptive motor control program comprises at least one of a dynamic braking mode, an active braking mode, or a coasting braking mode.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail, and is incorporated herein by reference in its entirety.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/235,972, entitled MOTORIZED SURGICAL INSTRUMENT, now U.S. Pat. No. 9,050,083.

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in one or more aspects of the present disclosure, a microcontroller may generally comprise a memory and a microprocessor ("processor") operationally coupled to the memory. The processor may control a motor driver circuit generally utilized to control the position and velocity of a motor, for example. In certain instances, the processor can signal the motor driver to stop and/or disable the motor, for example. In certain instances, the microcontroller may be an LM 4F230H5QR, available from Texas Instruments, for example. In at least one example, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available for the product datasheet.

It should be understood that the term processor as used herein includes any suitable microprocessor, or other basic computing device that incorporates the functions of a computer's central processing unit (CPU) on an integrated circuit or at most a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In at least one instance, the processor may be any single core or multicore processor such as those known under the trade name ARM Cortex by Texas Instruments. Nevertheless, other suitable substitutes for microcontrollers and safety processor may be employed, without limitation.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

Various instruments, tools, hubs, devices and/or systems, in accordance with the present disclosure, may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

One or more motor assemblies, as described herein, employ one or more electric motors. In various forms, the electric motors may be a DC brushed driving motor, for example. In other arrangements, the motor may include a brushless motor, a cordless motor, a synchronous motor, a stepper motor, or any other suitable electric motor. The electric motors may be powered by a power source that in one form may comprise a removable power pack. Batteries may each comprise, for example, a Lithium Ion ("LI") or other suitable battery. The electric motors can include rotatable shafts that operably interface with gear reducer assemblies, for example. In certain instances, a voltage polarity provided by the power source can operate an electric motor in a clockwise direction wherein the voltage polarity applied to the electric motor by the battery can be reversed in order to operate the electric motor in a counter-clockwise direction. In various aspects, a microcontroller controls the electric motor through a motor driver via a pulse width modulated control signal. The motor driver can be configured to adjust the speed of the electric motor either in clockwise or counter-clockwise direction. The motor driver is also configured to switch between a plurality of operational modes which include an electronic motor braking mode, a constant speed mode, an electronic clutching mode, and a controlled current activation mode. In electronic braking mode, two terminal of the drive motor are shorted and the generated back EMF counteracts the rotation of the electric motor allowing for faster stopping and greater positional precision.

As used in any aspect herein, a wireless transmission such as, for example, a wireless communication or a wireless transfer of a data signal can be achieved, by a device including one or more transceivers. The transceivers may include, but are not limited to cellular modems, wireless mesh network transceivers, Wi-Fi® transceivers, low power wide area (LPWA) transceivers, and/or near field communications transceivers (NFC). The device may include or may be configured to communicate with a mobile telephone, a sensor system (e.g., environmental, position, motion, etc.) and/or a sensor network (wired and/or wireless), a computing system (e.g., a server, a workstation computer, a desktop computer, a laptop computer, a tablet computer (e.g., iPad®, GalaxyTab® and the like), an ultraportable computer, an ultramobile computer, a netbook computer and/or a subnotebook computer; etc. In at least one aspect of the present disclosure, one of the devices may be a coordinator node.

The transceivers may be configured to receive serial transmit data via respective universal asynchronous receiver-transmitters (UARTs) from a processor to modulate the serial transmit data onto an RF carrier to produce a transmit RF signal and to transmit the transmit RF signal via respective antennas. The transceiver(s) can be further configured to receive a receive RF signal via respective antennas that includes an RF carrier modulated with serial receive data, to demodulate the receive RF signal to extract the serial receive data and to provide the serial receive data to respective UARTs for provision to the processor. Each RF signal has an associated carrier frequency and an associated channel bandwidth. The channel bandwidth is associated with the carrier frequency, the transmit data and/or the receive data. Each RF carrier frequency and channel bandwidth is related to the operating frequency range(s) of the transceiver(s). Each channel bandwidth is further related to the wireless communication standard and/or protocol with which the transceiver(s) may comply. In other words, each transceiver may correspond to an implementation of a selected wireless communication standard and/or protocol, e.g., IEEE 802.11 a/b/g/n for Wi-Fi® and/or IEEE 802.15.4 for wireless mesh networks using Zigbee routing.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

In this specification, unless otherwise indicated, terms "about" or "approximately" as used in the present disclosure, unless otherwise specified, means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

In this specification, unless otherwise indicated, all numerical parameters are to be understood as being prefaced and modified in all instances by the term "about," in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described herein should at least be construed in light of the number of reported significant digits and by applying ordinary rounding techniques.

Any numerical range recited herein includes all sub-ranges subsumed within the recited range. For example, a range of "1 to 10" includes all sub-ranges between (and including) the recited minimum value of 1 and the recited maximum value of 10, that is, having a minimum value equal to or greater than 1 and a maximum value equal to or less than 10. Also, all ranges recited herein are inclusive of the end points of the recited ranges. For example, a range of "1 to 10" includes the end points 1 and 10. Any maximum numerical limitation recited in this specification is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited. All such ranges are inherently described in this specification.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A surgical system, comprising:
    an end effector configurable between an open state and a clamped state, wherein the end effector comprises:
        a first jaw; and
        a second jaw moveable relative to the first jaw;
    a drive system, comprising:
        a motor; and
        a drive assembly movable by the motor to effect a tissue-treatment motion at the end effector; and
    a motor control system comprising motor control electronics, wherein the motor control system is configured to:
        receive an input signal from a sensor;
        deactivate or activate a motor drive signal transmitted from a power source based on the input signal;
        in response to the motor drive signal being activated, transmit the motor drive signal from the power source to the motor to control the motor to move the drive assembly to effect the tissue-treatment motion at the end effector; and
        in response to the motor drive signal being deactivated, adjust the motor control electronics to control the motor to modify the tissue-treatment motion based on the input signal.

2. The surgical system of claim 1, wherein the motor drive signal is based on a default control program.

3. The surgical system of claim 2, wherein the motor control electronics are controlled by an adaptive motor control program.

4. The surgical system of claim 3, wherein the adaptive motor control program comprises at least one of a dynamic braking mode, an active braking mode, or a coasting braking mode.

5. The surgical system of claim 1, wherein the motor control system comprises at least one sensor configured to measure at least one parameter of the drive system.

6. The surgical system of claim 5, wherein the motor control system controls the motor control electronics based on at least one reading of the at least one sensor.

7. The surgical system of claim 6, wherein the at least one parameter comprises a tissue creep parameter of the drive system, an inertia parameter of the drive system, or a friction loss parameter of the drive system.

8. A surgical system, comprising:
    an end effector configurable between an open state and a clamped state, wherein the end effector comprises:
        a first jaw; and
        a second jaw moveable relative to the first jaw;
    a drive system, comprising:
        a motor; and
        a drive assembly movable by the motor to effect a tissue-treatment motion at the end effector; and
    a motor control system, comprising:
        a motor drive circuit; and
        a motor control circuit configured to:
            receive an input signal from a sensor;
            deactivate or activate a motor drive signal transmitted from a power source based on the input signal;
            in response to the motor drive signal being activated, cause a transmission of the motor drive signal from the power source through the motor driver circuit to the motor to control the motor to move the drive assembly to effect the tissue-treatment motion at the end effector; and
            in response to the motor drive signal being deactivated, adaptively control elements of the motor drive circuit to control a deceleration of the motor in an absence of the motor drive signal.

9. The surgical system of claim 8, wherein the motor drive signal is based on a default control program.

10. The surgical system of claim 9, wherein the elements of the motor drive circuit are controlled by an adaptive motor control program.

11. The surgical system of claim 10, wherein the adaptive motor control program comprises at least one of a dynamic braking mode, an active braking mode, or a coasting braking mode.

12. The surgical system of claim 8, wherein the motor control system comprises at least one sensor configured to measure at least one parameter of the drive system.

13. The surgical system of claim 12, wherein the motor control system controls the elements of the motor drive circuit based on at least one reading of the at least one sensor.

14. The surgical system of claim 13, wherein the at least one parameter comprises a tissue creep parameter of the drive system, an inertia parameter of the drive system, or a friction loss parameter of the drive system.

15. A surgical system, comprising:
   an end effector configurable between an open state and a clamped state, wherein the end effector comprises:
      a first jaw; and
      a second jaw moveable relative to the first jaw;
   a drive system, comprising:
      a motor; and
      a drive assembly movable by the motor to effect a tissue-treatment motion at the end effector;
   a sensor; and
   a motor control system, comprising:
      a motor drive circuit; and
      a control circuit configured to:
         receive an input signal from the sensor;
         deactivate or activate a motor drive signal transmitted from a power source based on the input signal;
         in response to the motor drive signal being activated, cause a transmission of a motor drive signal from the power source through the motor drive circuit to the motor to control the motor to move the drive assembly to effect the tissue-treatment motion at the end effector;
         in response to the motor drive signal being deactivated, adjust the motor drive signal based on the input signal; and
         in response to the motor drive signal being deactivated, adaptively adjust elements of the motor drive circuit to control the motor in an absence of the motor drive signal based on the input signal.

16. The surgical system of claim 15, wherein adjusting the drive signal based on the input signal comprises deactivating the drive signal.

17. The surgical system of claim 16, wherein the control circuit is further configured to reactivate the drive signal.

18. The surgical system of claim 15, wherein the motor drive signal is based on a default control program.

19. The surgical system of claim 18, wherein the elements of the motor drive circuit are controlled by an adaptive motor control program.

20. The surgical system of claim 19, wherein the adaptive motor control program comprises at least one of a dynamic braking mode, an active braking mode, or a coasting braking mode.

* * * * *